US008349913B2

(12) United States Patent
Harren et al.

(10) Patent No.: US 8,349,913 B2
(45) Date of Patent: Jan. 8, 2013

(54) PROCESS FOR GENTLE MIXING AND COATING OF SUPERABSORBERS

(75) Inventors: Jörg Harren, Krefeld (DE); Herbert Vorholt, Haltern am See (DE); Manfred Van Stiphoudt, Kempen (DE); Rüdiger Hose, Tönisvorst (DE); Stephan Ramlow, Krefeld (DE); Stefan Derstappen, Tönisvorst (DE); Axel Busch, Krefeld (DE); Michael Lange, Rheinberg (DE); Waldemar Inger, Krefeld (DE); Kai Hebben, Tönisvorst (DE)

(73) Assignee: Evonik Stockhausen GmbH, Krefeld (DE)

( * ) Notice: Subject to any disclaimer, the term of this patent is extended or adjusted under 35 U.S.C. 154(b) by 644 days.

(21) Appl. No.: 12/600,964

(22) PCT Filed: May 21, 2008

(86) PCT No.: PCT/EP2008/004085
§ 371 (c)(1),
(2), (4) Date: Dec. 15, 2009

(87) PCT Pub. No.: WO2008/141821
PCT Pub. Date: Nov. 27, 2008

(65) Prior Publication Data
US 2010/0130950 A1    May 27, 2010

(30) Foreign Application Priority Data

May 22, 2007 (DE) .......................... 10 2007 024 080

(51) Int. Cl.
*C08L 15/00* (2006.01)
(52) U.S. Cl. ....................................................... 523/111
(58) Field of Classification Search .................. 523/111
See application file for complete search history.

(56) References Cited

U.S. PATENT DOCUMENTS

| 4,076,663 | A | 2/1978 | Masuda et al. |
| 4,131,576 | A | 12/1978 | Iovine et al. |
| 4,179,367 | A | 12/1979 | Barthell et al. |
| 4,286,082 | A | 8/1981 | Tsubakimoto et al. |
| 4,340,706 | A | 7/1982 | Obayashi et al. |
| 4,587,308 | A | 5/1986 | Makita et al. |
| 5,149,335 | A | 9/1992 | Kellenberger et al. |
| 5,409,771 | A | 4/1995 | Dahmen et al. |
| 5,610,220 | A | 3/1997 | Klimmek et al. |
| 5,672,633 | A | 9/1997 | Brehm et al. |
| 5,712,316 | A | 1/1998 | Dahmen et al. |
| 6,060,557 | A | 5/2000 | Dahmen et al. |
| 6,403,700 | B1 | 6/2002 | Dahmen et al. |
| 6,565,768 | B1 | 5/2003 | Dentler et al. |
| 6,605,673 | B1 | 8/2003 | Mertens et al. |
| 6,620,889 | B1 | 9/2003 | Mertens et al. |
| 6,831,142 | B2 | 12/2004 | Mertens et al. |
| 7,026,373 | B2 | 4/2006 | Smith et al. |
| 7,157,141 | B2 | 1/2007 | Inger et al. |
| 7,179,862 | B2 | 2/2007 | Mertens et al. |
| 7,285,599 | B2 | 10/2007 | Mertens et al. |
| 7,507,475 | B2 | 3/2009 | Inger et al. |
| 7,541,395 | B2 | 6/2009 | Reimann et al. |
| 2005/0171235 | A1 | 8/2005 | Harren et al. |
| 2006/0029567 | A1 | 2/2006 | Dutkiewicz |
| 2006/0029782 | A1 | 2/2006 | Harren et al. |
| 2007/0066754 | A1 | 3/2007 | Loeker et al. |
| 2007/0129495 | A1 | 6/2007 | Mertens et al. |
| 2008/0214740 | A1 | 9/2008 | Harren et al. |
| 2009/0209683 | A1 | 8/2009 | Reimann et al. |

FOREIGN PATENT DOCUMENTS

| DE | 2612846 | | 10/1976 |
| DE | 2706135 | A1 | 8/1978 |
| DE | 2840010 | A1 | 6/1979 |
| DE | 3503458 | A1 | 8/1985 |
| DE | 3713601 | A1 | 11/1988 |
| DE | 4020780 | C1 | 8/1991 |
| DE | 4244548 | A1 | 7/1994 |
| DE | 4418818 | A1 | 1/1995 |
| DE | 4333056 | A1 | 3/1995 |
| DE | 19529348 | A1 | 2/1997 |
| DE | 10334286 | A1 | 3/2005 |
| EP | 1757645 | A1 | 2/2007 |
| EP | 1757646 | A1 | 2/2007 |
| WO | 9605234 | A1 | 2/1996 |
| WO | 9934843 | A1 | 7/1999 |
| WO | 00/22017 | A1 | 4/2000 |
| WO | 02056812 | | 7/2002 |
| WO | 2004037903 | A2 | 5/2004 |
| WO | 2005011860 | A1 | 2/2005 |
| WO | 2005044900 | A1 | 5/2005 |

OTHER PUBLICATIONS

Jacek K. Dutkiewicz, "New Approach to Odor and pH Control in Personal Care," copyright 2006, Insight 2006, International Conference Oct. 29-Nov. 2, 2006.
U.S. Appl. No. 11/866,091, filed Oct. 2, 2007, Mertens et al.
U.S. Appl. No. 12/525,955, filed Sep. 4, 2009, Harren et al.
U.S. Appl. No. 12/575,071, filed Oct. 7, 2009, Fricker et al.
U.S. Appl. No. 12/575,124, filed Oct. 7, 2009, Fricker et al.
U.S. Appl. No. 12/575,146, filed Oct. 7, 2009, Fricker et al.
International Search Report filed on Feb. 6, 2009 in PCT/EP2008/004085.
Written Opinion filed on Feb. 6, 2009 in PCT/EP2008/004085.
U.S. Appl. No. 12/430,596, filed Apr. 27, 2009, Reimann et al.
International Preliminary Report on Patentability, mailed on Dec. 17, 2009 in PCT/EP2008/004085.

*Primary Examiner* — Edward Cain
(74) *Attorney, Agent, or Firm* — Smith Moore Leatherwood LLP; Philip P. McCann

(57) ABSTRACT

The present invention relates to a process for the production of a superabsorber, comprising as steps providing a water-absorbing polymer structure, bringing the water-absorbing polymer structure into contact with a modifying agent, preferably a modifying agent, and the further treatment of the water-absorbing polymer structure which has been brought into contact with the modifying agent. The further treatment is carried out at least partly in a rotating container. The invention furthermore relates to a device for the production of a superabsorber, superabsorbers, a composite, a process for the production of a composite, the composites obtainable by this process, chemical products, such as foams, shaped articles or fibers, and the use of a superabsorber.

17 Claims, 6 Drawing Sheets

PROCESS FOR GENTLE MIXING AND COATING OF SUPERABSORBERS

This application is a national stage application under 35 U.S.C. 371 of international application No. PCT/EP2008/004085 filed 21 May 2008, and claims priority to German Application No. DE 10 2007 024 080.7 filed 22 May 2007, the disclosures of which are expressly incorporated herein by reference.

BACKGROUND

The present invention relates generally to a process for the production of a superabsorber, a device for the production of a superabsorber, superabsorbers, a composite, a process for the production of a composite, the composites obtainable by this process, chemical products, such as foams, shaped articles or fibers, and the use of a superabsorber.

Superabsorbers are water-insoluble, crosslinked polymers which are capable of absorbing, and retaining under a certain pressure, large amounts of aqueous liquids, in particular body fluids, preferably urine or blood, with swelling and formation of hydrogels. Due to these characteristic properties these polymers are chiefly used for incorporation into sanitary articles, such as, for example, baby diapers, incontinence products or sanitary napkins.

Superabsorbers are as a rule produced by free-radical polymerization of monomers carrying acid groups in the presence of crosslinking agents. In this context polymers having different absorber properties can be prepared by the choice of the monomer composition, the crosslinking agent and the polymerization conditions and the processing conditions for the hydrogel obtained after the polymerization. Further possibilities are offered by the preparation of graft polymers, for example using chemically modified starch, cellulose and polyvinyl alcohol in accordance with DE-OS 26 12 846.

In order to optimize the properties, in particular the absorption properties, of superabsorbers for use in hygiene articles, the polymer particles obtained after comminution of the dried polymer gel are modified, preferably modified on the surface. During the surface modification a core-shell-like morphology may form, which is preferred in particular for superabsorber particles. This modification serves, for example, to provide the superabsorbers with odor-binding properties, to improve the dust properties of the superabsorbers, to reduce caking together of the superabsorber particles, to improve the absorption capacity of the superabsorbers under a pressure load and/or to influence advantageously the permeability properties of the superabsorber.

During these modification measures the superabsorbent polymer particles are brought into contact with a treatment agent, which can be present in a solution or dispersion or as a powder. In order to achieve as uniform as possible a treatment of the surface of the superabsorbers with the treatment agent, this bringing into contact is conventionally carried out by a procedure in which the superabsorber particles are initially introduced into a mixer and the treatment agent is then added with intensive mixing of the polymer particles. In the case of surface post-crosslinking as the surface modification measure, conventional mixing devices, such as, for example, the Patterson-Kelley mixer, the Schugi® vertical mixer (e.g. from Hosokawa with the trade name "Flexomix"), the DRAIS® turbulence mixer, the Lödige® mixer, the Ruberg® mixer, the screw mixer, the plate mixer or the fluidized bed mixer, are employed for this. Further suitable mixing devices are described, for example, in chapter 3.2.8.1 of the book "*Modern Superabsorbent Polymer Technology*" by F. L. Buchholz and A. T. Graham, Wiley-VCH, 1998.

In mixing devices which are conventionally employed, if aqueous solutions are employed as treatment agents the superabsorbers treated with these tend to form lumps immediately after leaving the mixing device. An inhomogeneous distribution of the treatment agent in or on the superabsorber is also often observed. In order to prevent such formation of lumps and to improve the homogenization, after leaving the mixing device the superabsorber is stored, for example, in conical silos and agitated by means of a rotating screw (cone mixer). The superabsorbers are stored in such a cone mixer until they are sufficiently relaxed and homogenized, and in particular have been converted from a ground-damp state which tends to stick together into a free-flowing state. Sufficient relaxation or homogenization is achieved, for example, when the superabsorber has reached a free-flowing state again. This is often the case when about the same flowability value which the superabsorbers showed before the addition of the aqueous treatment agent is reached. At this point in time the added liquid is distributed essentially homogeneously within the superabsorber particles, so that the difference between the water content in the core and the water content in the surface region (if charging is carried out with an aqueous treatment agent) of the polymer particles is increasingly compensated.

Disadvantages of such processes are, however, that a sufficient relaxation and homogenization can be achieved only very slowly, and in particular relatively large amounts of treated superabsorber cannot be processed. Due to these limitations the maximum amount of liquid which can be added to the superabsorber during the modification is also limited.

Furthermore, significant mechanical damage to the superabsorber may easily occur due to the rotating screw in the cone mixer or in other mixers of the rotor-stator principle, as a result of which the absorption properties are adversely influenced and in particular the dust content is increased.

SUMMARY

The present invention includes various embodiments as set forth herein.

The present invention is generally based on the object of overcoming the disadvantages resulting from the prior art.

In particular, it is an object of the present invention to provide a process by which absorbent polymers can be prepared, wherein particularly rapid and gentle relaxation and homogenization of a superabsorber which has been brought into contact with modifying agents, in particular with aqueous solutions as modifying agents, can be achieved.

According to one object according to the invention, this process should also render possible the production of superabsorbers employing large amounts of aqueous modifying solutions.

According to a further object according to the invention, the time expended to reach as homogeneous as possible a distribution of modifying agents or solutions not only between the water-absorbent polymer structures but also within these should be reduced.

The present invention was also based on the object of providing a process with which it is possible to produce superabsorbers having the lowest possible dust content.

The present invention was also based on the object of providing a device by means of which superabsorbers can also be produced with the use of large amounts of liquid during the modification. The device should also render possible the production of superabsorber amounts which are as high as possible in a given time interval. The dust content of the superabsorbers produced by this device should furthermore be as low as possible.

Generally, the categorizing claims make a contribution towards achieving at least one of the above-mentioned objects, the dependent claims presenting preferred embodiments.

DETAILED DESCRIPTION

A contribution towards achieving at least one of the above-mentioned objects is made by a process for the production of a superabsorber, comprising as steps:

a. provision of a water-absorbing polymer structure;
b. bringing the water-absorbing polymer structure into contact with a preferably aqueous modifying agent, preferably a surface-modifying agent;
c. further treatment of the water-absorbing polymer structure which has been brought into contact with the modifying agent;

wherein at least the further treatment in process step c) is carried out at least partly in a rotating container.

In step a) of the process according to the invention a water-absorbing polymer structure is first provided.

Preferred water-absorbing polymer structures provided in process step a) are fibers, foams or particles, fibers and particles being preferred and particles being particularly preferred.

Polymer fibers which are preferred according to the invention have dimensions such that they can be incorporated in or as yarns for textiles and also directly into textiles. It is preferable according to the invention for the polymer fibers to have a length in the range of from 1 to 500 mm, preferably 2 to 500 mm and particularly preferably 5 to 100 mm and a diameter in the range of from 1 to 200 denier, preferably 3 to 100 denier and particularly preferably 5 to 60 denier.

Polymer particles which are preferred according to the invention have dimensions such that they have an average particle size in accordance with ERT 420.2-02, incorporated herein by reference, in the range of from 10 to 3,000 μm, preferably 20 to 2,000 μm and particularly preferably 150 to 850 μm or 150 to 600 μm. In this context it is particularly preferable for the proportion of polymer particles having a particle size in a range of from 300 to 600 μm to be at least 30 wt. %, particularly preferably at least 40 wt. % and most preferably at least 50 wt. %, based on the total weight of the post-crosslinked water-absorbing polymer particles.

In a preferred embodiment of the water-absorbing polymer structures provided in process step a) these are based on ($\alpha$1) 20-99.999 wt. %, preferably 55-98.99 wt. % and particularly preferably 70-98.79 wt. % of polymerized, ethylenically unsaturated monomers carrying acid groups, or salts thereof, or polymerized, ethylenically unsaturated monomers containing a protonated or quaternized nitrogen, or mixtures thereof, mixtures comprising at least ethylenically unsaturated monomers containing acid groups, preferably acrylic acid, being particularly preferred, ($\alpha$2) 0-80 wt. %, preferably 0-44.99 wt. % and particularly preferably 0.1-44.89 wt. % of polymerized, monoethylenically unsaturated monomers which can be copolymerized with ($\alpha$1), ($\alpha$3) 0.001-5 wt. %, preferably 0.01-3 wt. % and particularly preferably 0.01-2.5 wt. % of one or more crosslinking agents, ($\alpha$4) 0-30 wt. %, preferably 0-5 wt. % and particularly preferably 0.1-5 wt. % of a water-soluble polymer, ($\alpha$5) 0-20 wt. %, preferably 2.5-15 wt. % and particularly preferably 5-10 wt. % of water, and ($\alpha$6) 0-20 wt. %, preferably 0-10 wt. % and particularly preferably 0.1-8 wt. % of one or more auxiliaries, the sum of the amounts by weight ($\alpha$1) to ($\alpha$6) being 100 wt. %.

The monoethylenically unsaturated monomers ($\alpha$1) containing acid groups can be partly or completely, preferably partly neutralized. Preferably the monoethylenically unsaturated monomers containing acid groups are neutralized to the extent of at least 25 mol %, particularly preferably to the extent of at least 50 mol % and moreover preferably to the extent of 50-80 mol %. Reference is made in this connection to DE 195 29348 A1, the disclosure of which is introduced herewith as reference. The neutralization can also take place partly or completely after the polymerization. Furthermore, the neutralization can be carried out with alkali metal hydroxides, alkaline earth metal hydroxides, ammonia and carbonates and bicarbonates. In addition, any further base which forms a water-soluble salt with the acid is conceivable. Mixed neutralization with various bases is also conceivable. Neutralization with ammonia and alkali metal hydroxides is preferred, particularly preferably with sodium hydroxide and with ammonia.

Furthermore, the free acid groups can predominate in a polymer, so that this polymer has a pH in the acid range. This acid water-absorbing polymer can be at least partly neutralized by a polymer having free basic groups, preferably amine groups, which is basic in comparison with the acid polymer. These polymers are called "mixed-bed ion exchange absorbent polymers" (MBIEA polymers) in the literature and are disclosed, inter alia, in WO 99/34843 A1. The disclosure of MBIEA polymers in WO 99/34843 A1 is incorporated herein by reference. As a rule, MBIEA polymers are a composition which comprises on the one hand basic polymers which are capable of exchanging anions, and on the other hand a polymer which is acid in comparison with the basic polymer and is capable of exchanging cations. The basic polymer contains basic groups and is typically obtained by polymerization of monomers which carry basic groups or groups which can be converted into basic groups. These monomers are above all those which contain primary, secondary or tertiary amines or the corresponding phosphines or at least two of the above functional groups. This group of monomers includes, in particular, ethyleneamine, allylamine, diallylamine, 4-aminobutene, alkyloxycyclins, vinylformamide, 5-aminopentene, carbodiimide, formaldacin, melamine and the like, and secondary or tertiary amine derivatives thereof.

Preferred ethylenically unsaturated monomers ($\alpha$1) containing acid groups are preferably those compounds which are mentioned as ethylenically unsaturated monomers ($\alpha$1) containing acid groups in WO 2004/037903 A2, which is introduced herewith as reference and thus forms part of the disclosure. Particularly preferred ethylenically unsaturated monomers ($\alpha$1) containing acid groups are acrylic acid and methacrylic acid, acrylic acid being most preferred.

According to one embodiment of the process according to the invention, untreated water-absorbing polymer structures in which the monoethylenically unsaturated monomers ($\alpha$2) which can be copolymerized with ($\alpha$1) are acrylamides, methacrylamides or vinylamides are employed.

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino (meth)acrylamide, dimethyl(meth)acrylamide or diethyl (meth)acrylamide. Possible vinylamides are, for example, N-vinylamides, N-vinylformamides, N-vinylacetamides, N-vinyl-N-methylacetamides, N-vinyl-N-methylformamides and vinylpyrrolidone. Among these monomers, acrylamide is particularly preferred.

According to another embodiment of the process according to the invention, water-absorbing polymer structures in which the monoethylenically unsaturated monomers ($\alpha 2$) which can be copolymerized with ($\alpha 1$) are water-soluble monomers are employed. In this connection alkoxypolyalkylene oxide (meth)acrylates, such as methoxypolyethylene glycol (meth)acrylates, are preferred in particular.

Water dispersible monomers are furthermore preferred as monoethylenically unsaturated monomers ($\alpha 2$) which can be copolymerized with ($\alpha 1$). Preferred water-dispersible monomers are acrylic acid esters and methacrylic acid esters, such as methyl (meth)acrylate, ethyl (meth)acrylate, propyl (meth) acrylate or butyl (meth)acrylate.

The monoethylenically unsaturated monomers ($\alpha 2$) which can be copolymerized with ($\alpha 1$) furthermore include methylpolyethylene glycol allyl ether, vinyl acetate, styrene and isobutylene.

Crosslinking agents ($\alpha 3$) which are preferably employed are those compounds which are mentioned as crosslinking agents ($\alpha 3$) in WO 2004/037903 A2. Among these crosslinking agents, water-soluble crosslinking agents are particularly preferred. In this context N,N'-methylenebisacrylamide, polyethylene glycol di(meth)acrylates, triallylmethylammonium chloride, tetraallylammonium chloride and allylnonaethylene glycol acrylate prepared with 9 mol of ethylene oxide per mol of acrylic acid are most preferred.

The polymer structures can comprise as water-soluble polymers ($\alpha 4$) water-soluble polymers such as partly or completely saponified polyvinyl alcohol, polyvinylpyrrolidone, starch or starch derivatives, polyglycols or polyacrylic acid, preferably in a polymerized-in form. The molecular weight of these polymers is not critical, as long as they are water-soluble. Preferred water-soluble polymers are starch or starch derivatives or polyvinyl alcohol. The water-soluble polymers, preferably synthetic polymers, such as polyvinyl alcohol, can also serve as a graft base for the monomers to be polymerized.

Auxiliaries ($\alpha 6$) which are contained in the polymer structures are, preferably, standardizing agents, odor-binding agents, surface-active agents or antioxidants and those additives which have been employed for the preparation of the polymer structures (initiators etc.).

In a particular embodiment of the water-absorbing polymer structures provided in process step a) these are based to the extent of at least 50 wt. %, preferably to the extent of at least 70 wt. % and moreover preferably to the extent of at least 90 wt. % on monomers which carry carboxylate groups. It is furthermore preferable according to the invention for component ($\alpha 1$) to consist of acrylic acid to the extent of at least 50 wt. %, preferably to the extent of at least 70 wt. %, this preferably being neutralized to the extent of at least 20 mol %, particularly preferably to the extent of at least 50 mol % and moreover preferably in a range of from 60 to 85 mol %.

The untreated, water-absorbing polymer structures can be prepared from the above-mentioned monomers, comonomers, crosslinking agents, water-soluble polymers and auxiliaries by various polymerization procedures. There may be mentioned by way of example in this connection bulk polymerization, which is preferably carried out in kneading reactors, such as extruders, solution polymerization, spray polymerization, inverse emulsion polymerization and inverse suspension polymerization.

Solution polymerization is preferably carried out in water as the solvent. The solution polymerization can be carried out continuously or discontinuously. A broad spectrum of possibilities of variation with respect to the reaction circumstances, such as temperatures, nature and amount of the initiators and also of the reaction solution, is to be found from the prior art. Typical processes are described in the following patent specifications: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818. The disclosures are introduced herewith as reference and therefore form part of the disclosure.

The polymerization is initiated by an initiator as is generally conventional. Initiators which can be used for initiation of the polymerization are all the initiators which form free radicals under the polymerization conditions and are conventionally employed in the preparation of superabsorbers. Initiation of the polymerization by the action of electron beams on the polymerizable aqueous mixture is also possible. Nevertheless, the polymerization can also be initiated in the absence of initiators of the above-mentioned type by the action of high-energy radiation in the presence of photoinitiators. Polymerization initiators can be contained in a solution of monomers according to the invention in dissolved or dispersed form. Possible initiators are all the compounds known to the person skilled in the art which dissociate into free radicals. These include, in particular, those initiators which have already been mentioned as possible initiators in WO 2004/037903 A2.

A redox system comprising hydrogen peroxide, sodium peroxodisulphate and ascorbic acid is particularly preferably employed for preparation of the water-absorbing polymer structures.

Inverse suspension and emulsion polymerization can also be used for preparation of the polymer structures. According to these processes an aqueous, partly neutralized solution of monomers ($\alpha 1$) and ($\alpha 2$), optionally containing water-soluble polymers and auxiliaries, is dispersed in a hydrophobic organic solvent with the aid of protective colloids and/or emulsifiers and the polymerization is started by free radical initiators. The crosslinking agents either are dissolved in the monomer solution and are metered together with this, or are added separately and optionally during the polymerization. The addition of a water-soluble polymer ($\alpha 4$) as a graft base is optionally carried out via the monomer solution or by direct initial introduction into the oily phase. The water is then removed azeotropically from the mixture and the polymer is filtered off.

Both in the case of solution polymerization and in the case of inverse suspension and emulsion polymerization, the crosslinking can furthermore be carried out by polymerizing in the polyfunctional crosslinking agent dissolved in the monomer solution and/or by reaction of suitable crosslinking agents with functional groups of the polymer during the polymerization steps. The processes are described, for example, in the publications U.S. Pat. No. 4,340,706, DE 37 13 601, DE 28 40 010 and WO 96/05234 A1, the corresponding disclosure directed to the process is incorporated herein by reference.

The hydrogels obtained after the polymerization in solution polymerization or inverse suspension and emulsion polymerization are dried in a further process step.

In the case of solution polymerization in particular, however, it is preferable for the hydrogels first to be comminuted before the drying. This comminution is carried out by comminution devices known to the person skilled in the art, such as, for example, a meat chopper.

Drying of the hydrogel is preferably carried out in suitable dryers or ovens. Rotary tube ovens, fluidized bed dryers, plate dryers, paddle dryers or infrared dryers may be mentioned by way of example. It is furthermore preferable according to the invention for the drying of the hydrogel to be carried out down to a water content of from 0.5 to 20 wt. %, preferably from 1 to 10 wt. %, the drying temperatures conventionally being in a range of from 100 to 200° C.

The water-absorbing polymer structures obtained after the drying can be ground again in a further process step, especially if they have been obtained by solution polymerization, and sieved off to the above-mentioned desired particle size. Grinding of the dried water-absorbing polymer structures is preferably carried out in suitable mechanical comminution devices, such as, for example, a roll mill or cutting mill.

According to another preferred embodiment, the water-absorbing polymer structures employed in process step a) are already post-crosslinked on the surface. During the surface post-crosslinking, the dried polymer structures or the not yet dried but preferably already comminuted hydrogel are brought into contact with a preferably organic chemical surface post-crosslinking agent. In this context the post-crosslinking agent, especially if it is not liquid under the post-crosslinking conditions, is preferably brought into contact with the polymer particles or the hydrogel in the form of a fluid $F_1$ comprising the post-crosslinking agent and a solvent. Solvents which are employed in this context are, preferably, water, water-miscible organic solvents, such as, for example, methanol, ethanol, 1-propanol, 2-propanol or 1-butanol or mixtures of at least two of these solvents, water being most preferred as the solvent. It is furthermore preferable for the post-crosslinking agent to be contained in the fluid $F_1$ in an amount in a range of from 5 to 75 wt. %, particularly preferably 10 to 50 wt. % and most preferably 15 to 40 wt. %, based on the total weight of the fluid $F_1$.

In the process according to the invention, the polymer structure or the comminuted hydrogel is preferably brought into contact with the fluid $F_1$ comprising the post-crosslinking agent by thorough mixing of the fluid $F_1$ with the polymer structure.

Suitable mixing units for application of the fluid $F_1$ are e.g. the Patterson-Kelley mixer, DRAIS® turbulence mixer, Lödige® mixer, Ruberg® mixer, screw mixers, plate mixers and fluidized bed mixers as well as continuously operating vertical mixers, in which the polymer structure is mixed by means of rotating blades in rapid frequency (Schugi® mixer).

During the post-crosslinking the polymer structure is preferably brought into contact with at most 20 wt. %, particularly preferably with at most 15 wt. %, moreover preferably with at most 10 wt. %, moreover still more preferably with at most 5 wt. % of solvent, preferably water.

In the case of polymer structures in the form of preferably spherical particles, it is furthermore preferable according to the invention for the components to be brought into contact in a manner such that merely the outer region, but not the inner region of the particulate polymer structures is brought into contact with the fluid $F_1$ and therefore the post-crosslinking agent.

Compounds which have at least two functional groups which can react with functional groups of a polymer structure in a condensation reaction (=condensation crosslinking agents), in an addition reaction or in a ring-opening reaction are preferably understood as post-crosslinking agents which are employed in the process according to the invention. Those post-crosslinking agents which have been mentioned as crosslinking agents of crosslinking agent classes II in WO 2004/037903 A2 are preferred as post-crosslinking agents in the process according to the invention.

Among these compounds, particularly preferred post-crosslinking agents are condensation crosslinking agents, such as, for example, diethylene glycol; triethylene glycol; polyethylene glycol; glycerol; polyglycerol; propylene glycol; diethanolamine; triethanolamine; polyoxypropylene; oxyethylene-oxypropylene block copolymers; sorbitan fatty acid esters; polyoxyethylene sorbitan fatty acid esters; trimethylolpropane; pentaerythritol; polyvinyl alcohol; sorbitol; 1,3-dioxolan-2-one (ethylene carbonate); 4-methyl-1,3-dioxolan-2-one (propylene carbonate); 4,5-dimethyl-1,3-dioxolan-2-one; 4,4-dimethyl-1,3-dioxolan-2-one; 4-ethyl-1,3-dioxolan-2-one; 4-hydroxymethyl-1,3-dioxolan-2-one; 1,3-dioxan-2-one; 4-methyl-1,3-dioxan-2-one; 4,6-dimethyl-1,3-dioxan-2-one and 1,3-dioxolan-2-one.

After the polymer structures or the hydrogels have been brought into contact with the post-crosslinking agent or with the fluid $F_1$ comprising the post-crosslinking agent they are heated to a temperature in the range of from 50 to 300° C., preferably 75 to 275° C. and particularly preferably 150 to 250° C., so that, preferably as a result of this, the outer region of the polymer structures is more highly crosslinked compared with the inner region (=post-crosslinking). The duration of the heat treatment is limited by the risk that the desired profile of properties of the polymer structures is destroyed as a result of the action of heat.

It is preferable according to the invention for the water-absorbing polymer structures provided in process step a) of the process according to the invention to have at least one of the following properties, preferably all of the following properties:

(β1) the maximum absorption according to ERT 440.2-02, incorporated herein by reference, of 0.9 wt. % strength aqueous NaCl solution is in a range of from at least 10 to 1,000, preferably from 15 to 500 and particularly preferably from 20 to 70 g/g;

(β2) the content according to ERT 470.2-02, incorporated herein by reference, which can be extracted with 0.9 wt. % strength aqueous NaCl solution is less than 30, preferably less than 20 and particularly preferably less than 10 wt. %, based on the absorbent polymer;

(β3) the bulk density according to ERT 460.2-02, incorporated herein by reference, is in the range of from 300 to 1,000, preferably 310 to 800 and particularly preferably 320 to 700 g/l, (β4) the pH according to ERT 400.2-02, incorporated herein by reference, of 1 g of the absorbent polymer in 1 l of water is in the range of from 4 to 10, preferably from 5 to 9 and particularly preferably from 5.5 to 7.5, (β5) the CRC value according to ERT 441.2-02, incorporated herein by reference, is in the range of from 10 to 100, preferably 15 to 80 and particularly preferably 20 to 60 g/g, (β6) the AAP value according to ERT 442.02, incorporated herein by reference, under a pressure of 20 g/cm2 is in the range of from 10 to 60, preferably 15 to 50 and particularly preferably 20 to 40 g/g.

The combinations of properties resulting from the above properties comprising two or more of these properties are in each case preferred embodiments of the water-absorbing polymer structure provided in process step a). Processes in which the water-absorbing polymer structure employed in process step a) has the properties or combinations of properties described in the following as letters or combinations of letters are furthermore particularly preferable as embodiments according to the invention: (β1), (β2), (β3), (β4), (β5), (β6) and (β1)(β2)(β3)(β4)(β5)(β6).

In step b) of the process according to the invention the water-absorbing polymer structures provided in process step a) and optionally already post-crosslinked on the surface are now brought into contact with a modifying agent, preferably a modifying agent.

According to a preferred embodiment of the process according to the invention, the modifying agent employed in process step b) is an agent chosen from the group consisting of pure solvents, such as, for example, water, a solution, a dispersion, an emulsion and a powder, the use of pure water, a solution, a dispersion and an emulsion being particularly preferred and the use of a solution being most preferred.

If the modifying agent is a solution, an emulsion or a dispersion it is furthermore preferable according to the invention for the modifying agent to comprise water to the extent of at least 10 wt. %, particularly preferably to the extent of at least 25 wt. % and most preferably to the extent of at least 50 wt. %, in each case based on the total weight of the modifying agent.

A solution employed as a modifying agent comprises at least one dissolved agent having a modifying action and a solvent. A dispersion employed as the modifying agent comprises at least one dispersed agent having a modifying action, as a solid, a dispersion agent and optionally a dispersing agent. An emulsion employed as a modifying agent comprises at least one emulsified agent having a modifying action, in the form of droplets of liquid, a liquid phase in which the droplets of liquid are distributed and optionally an emulsifier.

Water, water-miscible organic solvents, such as, for example, methanol, ethanol, 1,2-propanediol, 1-propanol or 2-propanol, or mixtures of water and water-miscible organic solvents, such as, for example, mixtures of water and methanol, mixtures of water and ethanol, mixtures of water and 1-propanol or mixtures of water and 2-propanol, are preferred as the solvent, as the dispersion agent and as the liquid phase, water being most preferred.

All the compounds known to the person skilled in the art which are suitable for influencing in particular the permeability, absorption, retention, dust or flow properties of water-absorbing polymer structures can be employed as agents having a modifying action which can be employed in particular as surface-modifying agents.

If water-absorbing polymer structures which are not post-crosslinked on the surface are employed in process step a) of the process according to the invention the agent having a modifying action can be a surface post-crosslinking agent, those compounds which have already been mentioned above as preferred post-crosslinking agents in connection with the surface post-crosslinking being preferred surface post-crosslinking agents.

The agent having a modifying action can furthermore be an organic salt comprising a divalent cation or cation of higher valency of a metal and at least one organic base as the anion. In this context it is preferable for the divalent cation or cation of higher valency of a metal to be chosen from the group consisting of $Mg^{2+}$, $Ca^{2+}$, $Ba^{2+}$, $Al^{3+}$, $Fe^{2+}$, $Fe^{3+}$, $Ga^{3+}$, $Ti^{4+}$, $Zr^{4+}$, $Cu^{2+}$ and $Zn^{2+}$, $Al^{3+}$ being most preferred. The organic base is preferably an at least partly deprotonated mono-, di- or tricarboxylic acid, deprotonated monocarboxylic acids being particularly preferred. Hydroxycarboxylic acids are furthermore preferred, at least partly deprotonated mono-, di- or hydroxytricarboxylic acids being preferred and monohydroxycarboxylic acids being particularly preferred.

Particularly preferred anions are, in particular, the corresponding bases of the following acids: anisic acid, benzoic acid, formic acid, valeric acid, citric acid, glyoxylic acid, glycollic acid, glycerolphosphoric acid, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidinoacetic acid, malic acid, isothionic acid, methylmaleic acid, adipic acid, itaconic acid, crotonic acid, oxalic acid, salicylic acid, gluconic acid, gallic acid, sorbic acid, gluconic acid, fatty acids, in particular stearic acid and adipic acid, and p-oxybenzoic acid. Among these bases, the most preferred are tartrate and lactate, lactate being preferred most of all. The organic salt which is most preferred in this connection is aluminium lactate.

The agent having a modifying action can also be an inorganic salt comprising a divalent cation or cation of higher valency of a metal and at least one inorganic anion. All metal salts known to the person skilled in the art can be employed as inorganic salts, but water-soluble metal salts are particularly preferred. In this context "water-soluble" is preferably understood as meaning metal salts of which preferably at least 1 g, particularly preferably at least 10 g, moreover preferably at least 100 g and most preferably at least 500 g are soluble in one liter of distilled water at a temperature of 25° C.

Among the above-mentioned, preferably water-soluble metal salts, sulphates, sulphites, sulphides, chlorides, bromides, iodides, nitrates, nitrites, phosphates, phosphites, carbonates, bicarbonates and hydroxides are preferred in particular, sulphates being most preferred.

It is furthermore preferable for the metal cation of the inorganic salt also to be a monovalent, divalent or a trivalent metal cation, trivalent metal cations also being most preferred here. Preferred metal cations are $N^{a+}$, $K^+$, $Li^+$, $Mg^{2+}$, $Ca^{2+}$, $Fe^{2+}$, $Fe^{3+}$, $Ag^+$, $Cu^+$, $Cu^{2+}$, $Zn^{2+}$ and $Al^{3+}$, $Al^{3+}$ being most preferred.

The following inorganic salts are particularly preferred as the agent having a modifying action: $AlCl_3 \times 6H_2O$, $NaAl(SO_4)_2 \times 12H_2O$, $Al(NO_3)_3 \times 9H_2O$, $KAl(SO_4)_2 \times 12H_2O$ or $Al_2(SO_4)_3 \times 14\text{-}18H_2O$ and the corresponding anhydrous salts, $Na_2SO_4$ or hydrates thereof, $MgSO_4 \times 10H_2O$ or anhydrous magnesium sulphate.

In this connection it may also be advantageous if in the case where a metal salt, in particular an inorganic metal salt, is employed as the agent having a modifying action this is employed in combination with an oxide of a metal as a further modifying agent. In this context all metal oxides can be employed as the oxide of a metal, "oxide of a metal" not being understood as meaning the oxides of half-metals, such as, for example, boron, silicon or germanium. These oxides of a metal particularly preferably comprise finely divided zinc oxide, which is based to the extent of at least 50 wt. % on optionally agglomerated particles having a particle size in a range of from about 10 nm to 500 µm. Such finely divided zinc oxides are obtainable, for example, under the trade name "Nanox®" from Elementis Specialties, USA.

The agent having a modifying action can furthermore be a thermoplastic polymer, it being preferable in this connection for the thermoplastic polymer to be employed in the form of a polymer dispersion. Preferred thermoplastic polymers are, in particular, polymers chosen from the group consisting of poly(meth)acrylates, (meth)acrylic acid copolymers, for example ethylene/(meth)acrylic acid copolymer, (meth) acrylic acid ester copolymers, maleic acid copolymers, for example maleic acid/propylene copolymers, polyurethanes, vinyl acetate copolymers, for example an ethylene/vinyl acetate copolymer or vinyl acetate/butyl acrylate copolymer, styrene copolymers, for example butyl acrylate/styrene copolymers, and polycarbonates. In this context the term (meth)acrylic acid represents the two compounds methacrylic acid and acrylic acid, of these two acrylic acid being particularly preferred. Thermoplastic polymers which are preferred according to the invention as regards the chemical composition of the polymers are furthermore all those thermoplastic polymers which are mentioned as thermoplastic polymers in DE-A-103 34 286 and in WO-A-2005/044900. The disclosure content of DE-A-103 34 286 and WO-A-2005/0044900 with respect to the thermoplastic polymers described therein is incorporated herein by reference.

The agent having a modifying action can furthermore be a protonated organic acid. Preferred protonated organic acids in this connection are anisic acid, benzoic acid, formic acid, valeric acid, citric acid, glyoxylic acid, glycollic acid, glycerolphosphoric acid, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidinoacetic acid, malic acid, isothionic acid, methylmaleic acid, adipic acid, itaconic acid, crotonic acid, oxalic acid, salicylic acid, gluconic acid, gallic acid, sorbic acid, gluconic acid, fatty acids, in particular stearic acid and adipic acid, and p-oxybenzoic acid, citric acid being most preferred.

Compounds which are furthermore possible agents having a modifying action are those comprising at least one anion and a polycation, in which the polycation has the structure I

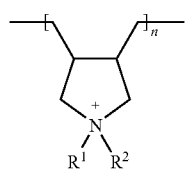

Structure I in which
R$^1$ and R$^2$ can be identical or different and represent a hydrocarbon radical having 1 to 10 carbon atoms, preferably 1 to 7 carbon atoms, particularly preferably 1 to 4 carbon atoms, moreover preferably 1 to 2 carbon atoms and most preferably a methyl group and
n has a value of at least 25, preferably at least 31, still more preferably at least 100, moreover preferably at least 1,000, still more preferably at least 2,000, moreover still more preferably at least 2,500, still more preferably at least 3,000 and most preferably at least 5,000.

Particularly preferred polycations of structure I are polydiallyldimethylamines. Preferred anions are the chloride ion, the bromide ion, the iodide ion, the sulphide ion, the sulphate ion, the sulphite ion, the nitrate ion, the nitrite ion, the acetate ion, the lactate ion, the carbonate ion, the bicarbonate ion, the phosphate ion, the phosphite ion and the hydroxide ion. In addition to these mono- and divalent anions the compound can also comprise polyvalent anions. A particularly preferred compound composing at least one anion and a polycation is a polymer of diallyldimethylammonium chloride having a value for n of at least 25, preferably at least 31, moreover preferably at least 100, moreover still more preferably at least 1,000, further preferably at least 2,500 and most preferably at least 5,000. Compounds which are based on polyallylamines and polyvinylamines particularly preferably fall under the present group.

The agent having a modifying action can also be inorganic or organic fine particles, in this case the agent having a modifying action preferably being employed in the form of a dispersion. In another embodiment according to the invention the fine particles are employed as such, usually in the form of a separate addition. In this case a binder can also be employed before or also after this addition of the fine particles or before and after this addition, for which, for example, one or more of the agent groups listed above or in the following are suitable. Preferred organic or inorganic fine particles are those fine particles which are mentioned as preferred organic or inorganic fine particles in WO 2005/011860 A1. SiO compounds, in particular pyrogenic silica, such as is obtainable, for example, under the trade name Aerosil®, precipitated silicas, such as are commercially obtainable under the name Sipernat®, or silica sol, such as is obtainable, for example, under the trade name Levasil®, are particularly preferred as the inorganic fine particles. Preferred organic fine particles are powders based on polysaccharides, for example particles of cellulose or cellulose derivatives, particles of starch or starch derivatives or cyclodextrin particles.

Water-soluble polymers are also possible as a further agent having a modifying action. Preferred water-soluble polymers are, in particular, polyvinyl alcohols or water-soluble polyethylene glycols. The modular weight of these water-soluble polymers is preferably in a range of from 200 to 100,000 g/mol, particularly preferably in a range of from 300 to 50,000 g/mol and most preferably in a range of from 350 to 350,000 g/mol.

In addition to one or more substances which reduce odor formation, such as are described, inter alia, in "*New Approach to Odor and pH Control in Personal Care*", Jacek K. Dutklewicz, Insight 2006, International Conference Oct. 29-Nov. 2, 2006 and in US 2006/0029567 A1, the descriptions of substances which reduce odor formation are incorporated herein by reference, compounds of the structure II

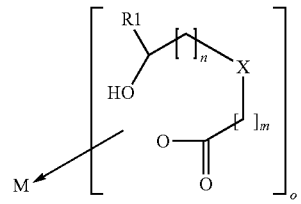

Structure II where
R1 is a $C_1$-$C_{20}$-, preferably a $C_1$-$C_{15}$- and moreover preferably a $C_3$-$C_{10}$-hydrocarbon;
X is not present (in this case there is a direct carbon-carbon bond between the carbon in [ ]$_n$ and the carbon in [ ]$_m$ or is a double bond system containing in a range of from 1 to 5, preferably in a range of from 1 to 3 double bonds or particularly preferably a single double bond, and in the case of at least 2 double bonds preferably a conjugated double bond system;
M is a charged or non-charged, preferably charged metal;
m is in a range of from 1 to 15, preferably in a range of from 3 to 12 and moreover preferably in a range of from 5 to 9;
n is in a range of from 1 to 5, preferably in a range of from 1 to 3 and moreover preferably 1;
o is in a range of from 1 to 4, preferably in a range of from 1 to 3 and particularly preferably in a range of from 1 to 2 and moreover preferably 2,
are possible as the agent having a modifying action.

In this context these compounds of structure II can advantageously be employed as an agent having a modifying action in combination with an amino acid, preferably with methionine, arginine and cysteine, particularly preferably with cysteine or arginine.

Pure water can also be employed as the modifying agent, for example for subsequent moistening of the water-absorbing polymer structures.

Two, three, four or more of the variants of an agent having a modifying action or a modifying agent mentioned above can furthermore be employed in combination with one another.

Modifying agents which are particularly preferred according to the invention and which can be employed in particular as surface-modifying agents are one, two or more chosen from the group consisting of
i) an aqueous solution comprising water and at least one surface post-crosslinking agent dissolved in water;
ii) an aqueous solution comprising water and at least one water-soluble polymer dissolved in water, particularly preferably a polyethylene glycol, in particular having a molecular weight in a range of from 300 to 15,000 g/mol;
iii) an aqueous suspension comprising water, a protonated organic acid, preferably citric acid, and inorganic fine particles, preferably an SiO compound, particularly preferably a precipitated silica;
iv) an aqueous solution comprising water and at least one organic metal salt, preferably aluminium lactate;
v) an aqueous solution comprising water, at least one surface post-crosslinking agent dissolved in water and an organic metal salt, preferably aluminium lactate;
vi) an aqueous solution comprising water and an inorganic metal salt, preferably aluminium sulphate;
vii) an aqueous solution comprising water, at least one surface post-crosslinking agent and an inorganic metal salt, preferably aluminium sulphate;
viii) an inorganic powder, preferably an inorganic metal salt, particularly preferably aluminium sulphate, aluminium chloride or aluminium phosphate, or an SiO compound, preferably a pyrogenic silica or a precipitated silica;
ix) an organic powder, preferably a powder based on polysaccharides, for example carboxycellulose particles, or cyclodextrin particles;
x) an aqueous dispersion comprising water, at least one inorganic or organic metal salt, preferably aluminium sulphate or aluminium lactate, and at least one oxide of a metal, preferably a zinc oxide;
xi) an aqueous dispersion comprising water, at least one surface post-crosslinking agent, at least one inorganic or organic metal salt, preferably aluminium sulphate or aluminium lactate, and at least one oxide of a metal, preferably a zinc oxide;
xii) an aqueous solution comprising water and at least one polycation, preferably a polydiallyldimethylammonium chloride;
xiii) an aqueous solution comprising water, at least one surface post-crosslinking agent and at least one polycation, preferably a polydiallyldimethylammonium chloride;
xiv) an aqueous dispersion comprising water and a thermoplastic polymer dispersed in water;
xv) an aqueous dispersion comprising water, at least one surface post-crosslinking agent and a thermoplastic polymer dispersed in water;
xvi) an aqueous solution or an aqueous dispersion comprising a compound of structure II, preferably a product of Goldschmidt GmbH obtainable under the trade name "Tegosorb®", water and optionally inorganic fine particles, preferably an SiO compound, particularly preferably a precipitated silica;
xvii) water, in particular distilled water, water deionized by means of an ion exchanger or tap water;
xviii) aqueous solutions or aqueous suspensions based on organic solids, preferably powders based on polysaccharides, for example carboxycellulose particles, or cyclodextrin particles.

It is furthermore preferable according to the invention for the agent having a modifying action to be brought into contact with the water-absorbing polymer structure in process step b) in an amount in a range of from 0.001 to 20 wt. %, particularly preferably 0.001 to 10 wt. % and most preferably 0.01 to 5 wt. %, based on the weight of the water-absorbing polymer structure, the amount of agent having a modifying action employed depending decisively on the nature of the agent. It is furthermore preferable for the water-absorbing polymer structure to be brought into contact with water in process step b) in an amount in a range of from 0.5 to 30 wt. %, particularly preferably 1 to 20 wt. % and most preferably 1.5 to 10 wt. %, in each case based on the weight of the water-absorbing polymer structures.

The modifying agent is preferably brought into contact with the water-absorbing polymer structures in process step b) by mixing in mixing devices known to the person skilled in the art, preferably in a Patterson-Kelley mixer, a DRAIS® turbulence mixer, a Lödige® mixer, a Ruberg® mixer, a screw mixer, a plate mixer, a fluidized bed mixer or in a continuously operating vertical mixer in which the polymer structure is mixed by means of rotating blades in a high frequency (Schugi® mixer). The average dwell time of the water-absorbing polymer structures, which have been brought into contact with the modifying agent, in these mixers is preferably in a range of from 0.01 to 240 seconds, particularly preferably in a range of from 0.05 to 180 seconds and most preferably in a range of from 0.1 to 120 seconds.

In process step c) of the process according to the invention the water-absorbing polymer structure which has been brought into contact with the modifying agent is now further treated, the further treatment in process step c) being at least partly carried out in a rotating container. The further treatment in process step c) is preferably a mixing of the water-absorbing polymer structure which has been brought into contact with the modifying agent.

According to a preferred embodiment of the process according to the invention, the water-absorbing polymer structures which have been brought into contact with the modifying agent and are employed in process step c) are characterized by a moisture content, determined in accordance with ERT 430.2-02, incorporated herein by reference, of at most 30 wt. %, preferably at most 25 wt. %, still more preferably at most 20 wt. % and most preferably at most 15 wt. %, in each case based on the total weight of the water-absorbing polymer structure.

If the bringing into contact of the water-absorbing polymer structure with the modifying agent in process step b) has not already taken place in a rotating container, the water-absorbing polymer structure which has been brought into contact with the modifying agent is first transferred into a rotating container.

The rotating container preferably comprises a horizontally mounted container constructed like a drum, which can be made to rotate around an axis running horizontally through the middle of the container by means of suitable motors. Along this axis the container comprises a rear top region, a front top region and a jacket region connecting the rear and front top region. In principle, the container can be made of plastic or also of steel, but the container is preferably made of high-grade steel, it being possible for the internal surfaces of the container which may come into contact with the water-absorbing polymer structure optionally to be coated with suitable polymers, for example with polypropylene or poly (tetrafluoroethylene) polymers. The container is preferably cylindrical in configuration, it being possible for the rear and the front top region optionally to be dome-like in construction. The cylindrical configuration also includes those in which the jacket region is not strictly cylindrical in configuration, for example is configured as a bulged or curved form or with an hourglass-like constriction.

The diameter of the container is preferably in a range of from 1 meter to 15 meters, particularly preferably 2 meters to 10 meters and most preferably 2.5 meters to 5 meters, while the length of the container is preferably in a range of from 1 meter to 20 meters, particularly preferably 2 meters to 10 meters and most preferably 3 meters to 7 meters. The filling volume of the rotating container is preferably in a range of from 100 to 250,000 liters, particularly preferably 1,000 to 100,000 liters and most preferably 5,000 to 50,000 liters.

Mixing aids, which likewise can be made of plastic or metal, but are preferably constructed from high-grade steel, and can optionally also be coated with suitable polymers, for example with polypropylene or poly(tetrafluoroethylene) polymers, and are configured as paddles are preferably attached to the insides of the container which come into contact with the water-absorbing polymer structure. It is furthermore preferable for the mixing aids to be fixed permanently to the insides of the container, fixing with the jacket region of the container being most preferred. It is furthermore preferable for the mixing aids to be constructed in a dish shape. The number of mixing aids within the container is preferably in a range of from 1 to 50, particularly preferably 2 to 25 and most preferably 3 to 6.

The advantage of the use of such a rotating container is, for example, that the total contents of the container can be moved and restratified by the mixing aids at any time, the water-absorbing polymer structure being moved within the container along a loop-like path. Since there are preferably no movable or counter-rotating parts in the entire container, apart from a possibly movable inlet and outlet device, the water-absorbing polymer structure is subjected to only a slight friction, if any, during the rotation of the container. A grinding effect which is often observed in the cone mixers conventionally employed or in other stator-rotor mixers arises to only a very reduced extent, if at all.

According to a further embodiment according to the invention, the rotating container furthermore comprises, in the front top region, a product inlet which can optionally be equipped with inlet aids, such as screws, slide valves, shakers, cellular wheel sluices or sources of compressed air or a combination of at least two of these, via which the water-absorbing polymer structure which has been brought into contact with the modifying agent can be introduced into the rotating container, and a preferably regulatable product outlet, via which the water-absorbing polymer structure treated in the container can be discharged from the rotating container. The container can be made to rotate via suitable electric motors, the speed of rotation preferably being in a range of from 1 to 100 revolutions per minute, particularly preferably 2 to 50 revolutions per minute and most preferably 3 to 15 revolutions per minute.

The rotating container furthermore preferably comprises, as an outlet unit, a lance which can preferably be inserted through the middle of the rear top region along the axis of rotation of the rotating container, it being possible for this lance likewise to be made of plastic or metal, but preferably being constructed from high-grade steel. It is furthermore preferable for the lance not to be permanently connected to the rotatable container, that is to say for the lance not to rotate about its longitudinal axis when the container is also made to rotate. A discharge element, in which a depression is preferably constructed to accommodate or guide substances and over which the water-absorbing polymer structure is passed in the direction of the outlet, can be attached to the lance inside the container. By fixing this discharge element to the movable lance, the discharge element is also arranged movably inside the container.

The rotating container can furthermore comprise, as one of the inlet units, a feed for a modifying agent, this feed preferably being attached in the front top region. This feed is preferably a spray nozzle arranged inside the rotating container, preferably on the front often static top region and preferably fixed, via which liquids in particular, for example solutions, dispersions or an emulsion, but optionally also solids, such as, for example, powder, can be applied to the water-absorbing polymer structure.

According to a particularly preferred embodiment of the process according to the invention, a mixing device from Lindor, Dordrecht, The Netherlands is employed in process step c), this mixing device preferably being on a mixing device chosen from the group consisting of the mixing devices Lindor 70, Lindor 200, Lindor 500, Lindor 750, Lindor 1000, Lindor 1500, Lindor 2000, Lindor 2300, Lindor 4000, Lindor 7000, Lindor 8000, Lindor 12000, Lindor 14000 and Lindor 25000. The above-mentioned types can be designed for continuous operation with respect to their inlet and outlet equipment. In addition to a start-up and shutdown phase, continuous operation preferably exists according to the invention if an uninterrupted introduction into and discharge from the container takes place over a period of at least 1, preferably at least 2 and particularly preferably at least 10 hours after the start-up phase, which usually takes place as filling.

According to a further particular embodiment of the process according to the invention, the rotating container employed in process step c) can comprise a heating or cooling device which renders it possible to at least partly heat or cool the water-absorbing polymer structure present in the rotating container. In this context, it may be advantageous if this heating or cooling device heats or cools at least a part of the jacket region of the rotating container and the jacket region heated or cooled in this way then passes on the heat to the water-absorbing polymer structure or absorbs the heat of the water-absorbing polymer structure. In the case of a heating device, the use of heat sources, for example infrared lamps, inside the rotating container or the introduction of hot gases, such as, for example, hot air, is also possible in particular. In this context, it may be advantageous in particular to limit the heating or the cooling of the water-absorbing polymer structure to a defined region between the front and the rear top region of the rotating container.

The average dwell time (which is calculated from the quotient of the volume of the rotatable container and the volume flow fed in) of the water-absorbing polymer structure in the rotating container is preferably in a range of from 5 to 300 minutes, particularly preferably in a range of from 10 to 180 minutes and most preferably in a range of from 15 to 140 minutes. It is also preferable for the container to be filled in process step c) to a maximum of 80% of its largest cross-sectional area (which means that cross-sectional area passed through by the perpendicular of the axis of rotation), particularly preferably a maximum of 70%, still more preferably a maximum of 60% and most preferably a maximum of 50% and furthermore preferably a maximum of 40%. Thus, as a rule a maximum of 60 vol. %, preferably a maximum of 55 vol. %, preferably a maximum of 50 vol. % and moreover preferably 40 vol. % of the internal volume of the container is filled.

According to a particularly preferred embodiment of the process according to the invention the further treatment in process step c) is carried out at least partly continuously. This is realized, for example, in that the water-absorbing polymer structure which has been brought into contact with the modifying agent is introduced via the inlet in the front top region of the rotating container, flows through the rotating container and then, after a certain dwell time, leaves the rotating container via the outlet at the rear top region. In this context the average dwell time of a water-absorbing polymer particle depends inter alia on the amount of water-absorbing polymer structure which has been brought into contact with the modifying agent fed per unit time via the inlet, on the volume of the rotating container and on the amount of treated water-absorbing polymer structure exiting via the outlet per unit time. The advantage of a continuous operation of a rotating mixer for treatment of the comparatively large amount of water-absorbing polymer structure which as a rule has been brought into contact with a comparatively small amount of modifying agent lies in particular in that a very rapid distribution of the modifying agent in the water-absorbing polymer structure occurs. This is the case in particular if the water-absorbing polymer structure or also the mixture of modifying agent and water-absorbing polymer structure is ground-damp and therefore tends to adhere or to form lumps. Regulation of the amounts flowing to the container can be rendered possible in particular by an adjustable outlet device, in addition to an adjustable inlet device. This outlet device preferably has an adjustable outlet opening. Possible outlet devices are, in addition to a weir, preferably a vertically adjustable weir, also cellular wheel sluices, discharge screws, which can be frequency-regulated in particular, or at least two of these.

In particular, if the treatment in process step c) is carried out continuously it has also proved advantageous if an outlet device having a variable outlet opening, which is preferably configured like a weir, is provided in the region of the outlet at the rear top region. It is preferable here to construct in the outlet opening a weir, the cross-sectional area of which corresponds to the cross-sectional area of the outlet, it being possible for the cross-sectional area of the weir to be reduced mechanically or also electromechanically. When the cross-sectional area of the weir corresponds to the cross-sectional area of the outlet, the outlet is closed and the water-absorbing polymer structure cannot leave the rotating container. When the cross-sectional area of the weir is now reduced, for example, in the case of a circular weir attached in a circular outlet, by rotating the upper half of the circle around an axis running through the middle of the circular weir, the water-absorbing polymer structure can leave the rotating container through the gap formed in this way. The outlet can therefore be regulated via the weir. Via regulation of the cross-sectional area, in particular in the case of continuous treatment of the water-absorbing polymer structure in process step c), the average dwell time of the water-absorbing polymer structure in the rotating container can vary.

According to a particular embodiment of the process according to the invention, it is furthermore also conceivable for the water-absorbing polymer structure to be brought into contact with the modifying agent in process step b) at least partly likewise in a rotating container. In this case, process steps b) and c) are carried out at least partly simultaneously in that any water-absorbing polymer structure which has not yet been brought into contact at all with a modifying agent or a water-absorbing polymer structure which has already partly been brought into contact with a modifying agent is introduced into the rotating container via the inlet, the water-absorbing polymer structure is then sprayed with the modifying agent, preferably by means of a nozzle, by a feed inside the container, preferably in the region of the front top region, and the water-absorbing polymer structure which has been sprayed with the modifying agent is then further treated by mixing in the rotating container.

Embodiments of the process for the production of a superabsorber which are particularly preferred according to the invention are chosen from the following processes:

(γ1) A water-absorbing polymer structure which has been brought into contact with less than 25 wt. %, preferably less than 10 and particularly preferably less than 5 wt. %, in each case based on the modifying agent or agents employed, or furthermore preferably has not yet been brought into contact at all with a modifying agent is introduced into the rotating mixer, is brought into contact there, preferably in the front top region, with a modifying agent and is then further treated by mixing in the rotating container, it being possible, especially in the cases where the modifying agent comprises a post-crosslinking agent, for the water-absorbing polymer structure also to be heated inside the rotating container. Possible modifying agents in this embodiment of the process according to the invention are, in particular, all the above-mentioned modifying agents i) to xvii), by themselves or as a combination of at least two of these.

(γ2) A process according to (γ1), but wherein a water-absorbing polymer structure which is already post-crosslinked on the surface is employed. Possible modifying agents in this embodiment of the process according to the invention are, in particular, the above-mentioned modifying agents ii), iii), iv), vi), viii), ix), x), xii), xiv), xvi) and xvii), by themselves or as a combination of at least two of these.

(γ3) A water-absorbing polymer structure which has been brought into contact with less than 25 wt. %, preferably less than 10 and particularly preferably less than 5 wt. %, in each case based on the modifying agent or agents employed, or furthermore preferably has not yet been brought into contact at all with a modifying agent is brought into contact with a modifying agent by mixing before it is introduced into the rotating mixer. Possible modifying agents in this embodiment of the process according to the invention are, in particular, the above-mentioned modifying agents i) to xvii), by themselves or as a combination of at least two of these.

(γ4) A process according to (γ3), but wherein a water-absorbing polymer structure which has already been post-crosslinked on the surface is employed. Possible modifying agents in this embodiment of the process according to the invention are, in particular, the above-mentioned modifying agents ii), iii), iv), vi), viii), ix), x), xii), xiv), xvi) and xvii), by themselves or as a combination of at least two of these.

(γ5) A water-absorbing polymer structure which has not yet been brought into contact at all with a modifying agent is introduced into the rotating mixer, is preferably brought into contact there in the front top region with a first modifying agent and is then further treated by mixing in the rotating container, it being possible, especially in cases where the first modifying agent comprises a post-crosslinking agent, for the water-absorbing polymer structure also to be heated inside the rotating container. In a region downstream of the addition of the first modifying agent the water-absorbing polymer structure is then brought into contact with a second modifying agent and is then further treated again. In this context the water-absorbing polymer structure can be brought into contact with the first and the second modifying agent and the subsequent further treatment can be carried out in one and the same rotating container. However, it is also conceivable to employ two or more rotating containers connected in series. All the above-mentioned modifying agents i) to xvii), by themselves or as a combination of at least two of these, are possible in particular as the first modifying agent in this embodiment of the process according to the invention, while the modifying agents ii), iii), iv), vi), viii), ix), x), xii), xiv), xvi) or xvii), by themselves or as a combination of at least two of these, can preferably be employed as the second modifying agent.

(γ6) A process according to (γ5), but wherein a water-absorbing polymer structure which has already been post-crosslinked on the surface is employed. The above-mentioned modifying agents ii), iii), iv), vi), viii), ix), x), xii), xiv) and xvi), by themselves or as a combination of at least two of these, are possible in particular as the first and as the second modifying agent in this embodiment of the process according to the invention.

The superabsorbers according to the invention are preferably characterized by a dust content, determined in accordance with the test method described herein, of at most 8, particularly preferably at most 6, moreover still more preferably of at most 4 and most preferably of at most 2.

It is furthermore preferable according to the invention for the superabsorbers according to the invention to have a moisture content, determined in accordance with ERT 430.2-02, in a range of from 2 to 10 wt. %, particularly preferably 2 to 8 wt. %, still more preferably 2 to 6 wt. % and most preferably 2 to 5 wt. %. If the moisture content is outside the range of from 2 to 10 wt. %, the absorption and conveying properties of the superabsorber are adversely influenced. In this context the moisture content stated above for the superabsorber can correspond to that moisture content which the superabsorber has after its production, and in particular before its incorporation into a hygiene article. However, the moisture content can also correspond to that moisture content which the superabsorber has when it is isolated from a hygiene article, for example a diaper. Since the superabsorber, when it has already been incorporated into a hygiene article, may have already absorbed water, which is always contained in the ambient air in the form of water vapor, it is entirely possible for the moisture content of a superabsorber in a hygiene article, where appropriate, to exceed the upper limit value of 10 wt. %.

A contribution towards achieving at least one of the above-mentioned objects is also made by a device for the production of a superabsorber comprising, connected to one another by fluid lines:
 a polymerization region; followed by
 a drying region; followed by
 a further treatment region;
 wherein the further treatment region comprises a rotatable container.

The polymerization region preferably comprises a polymerization device, it being possible for all the devices known to the person skilled in the art which can be employed for the preparation of polymer gels based on polyacrylates to be employed as the polymerization device, continuously operating polymerization devices, such as, for example, polymerization belts, being particularly preferred. Suitable polymerization devices are described, for example, in paragraph 3.2.3 in "*Modern Superabsorbent Polymer Technology*" by F. L. Buchholz and A. T. Graham, Wiley-VCR, 1998.

The drying region preferably comprises a drying device, it likewise being possible for all the drying devices known to the person skilled in the art to be employed as the drying device. Preferred drying devices include, in particular, rotary tube ovens, fluidized bed dryers, plate dryers, paddle dryers and infrared dryers.

It is furthermore advantageous for the polymerization region also to comprise a gel-comminuting region comprising a gel comminution device, such as, for example, a meat chopper or a cutting blade, so that the gel can also be comminuted before the drying. A more efficient drying of the polymer gel is possible in this manner. Suitable gel comminution devices are described, for example, in paragraph 3.2.4 in "*Modern Superabsorbent Polymer Technology*" by F. L. Buchholz and A. T. Graham, Wiley-VCR, 1998. It may also be advantageous if the drying region also comprises a grinding device and/or a sieving device, in addition to the drying device, so that the water-absorbing polymer structures can also be comminuted and/or sieved off to a particular particle size, preferably to a particle size in a range of from 150 to 850 μm, before entry into the further treatment region. Suitable grinding devices and sieving devices are described, for example, in paragraph 3.2.6 in "*Modern Superabsorbent Polymer Technology*" by F. L. Buchholz and A. T. Graham, Wiley-VCH, 1998.

It may furthermore be advantageous if a post-crosslinking reactor is also arranged between the further treatment region and the drying region, so that the water-absorbing polymer structures can also be post-crosslinked on the surface before entry into the further treatment region. Suitable post-crosslinking reactors are described, for example, in paragraph 3.2.8.1 in "*Modern Superabsorbent Polymer Technology*" by F. L. Buchholz and A. T. Graham, Wiley-VCH, 1998.

The further treatment region preferably comprises a rotating container, those containers which have already been described above in connection with the process according to the invention being preferred as the rotating container.

According to a particularly preferred embodiment of the device according to the invention, the further treatment region comprises at least one further mixer upstream of the rotatable container, this further mixer preferably being a Kelley mixer, DRAIS® turbulence mixer, Lodige® mixer, Ruberg® mixer, screw mixer, plate mixer, fluidized bed mixer or a continuously operating vertical mixer in which the polymer structure is mixed by means of rotating blades in rapid frequency (Schugi® mixer). In this upstream mixer, the water-absorbing polymer structures can already be brought into contact with a modifying agent before entry into the rotating container.

A contribution towards achieving the above-mentioned objects is also made by a process for the production of a superabsorber in which a device described above is employed.

A further contribution towards achieving the above-mentioned object is made by a superabsorber which is obtainable by the process according to the invention described above.

A further contribution towards achieving the objects described above is made by a composite comprising the superabsorbers according to the invention or the superabsorbers obtainable by the process according to the invention and a substrate. In this context it is preferable for the superabsorbers according to the invention and the substrate to be firmly bonded to one another. Preferred substrates are films of polymers, such as, for example, of polyethylene, polypropylene or polyamide, metals, nonwovens, fluff, tissues, woven fabric, natural or synthetic fibers, or other foams. It is furthermore preferable according to the invention for the composite to include at least one region which comprises the superabsorber according to the invention in an amount in the range of from about 15 to 100 wt. %, preferably about 30 to 100 wt. %, particularly preferably from about 50 to 99.99 wt. %, furthermore preferably from about 60 to 99.99 wt. % and moreover preferably from about 70 to 99 wt. %, in each case based on the total weight of the region in question, this region preferably having a size of at least 0.01 cm$^3$, preferably at least 0.1 cm$^3$ and most preferably at least 0.5 cm$^3$.

In a particularly preferred embodiment of the composite according to the invention, this is a sheet-like composite such as is described as "absorbent material" in WO 02/056812 A1. The disclosure content of WO 02/056812 A1, with respect to the precise structure of the composite, the weight per unit area of it constituents and its thickness, is incorporated herein by reference.

A further contribution towards achieving at least one of the above-mentioned objects is made by a process for the production of a composite, wherein the superabsorbers according to the invention or the superabsorbers obtainable by the process according to the invention and a substrate and optionally an additive are brought into contact with one another. Substrates which are preferably employed are those substrates which have already been mentioned above in connection with the composite according to the invention.

A contribution towards achieving at least one of the above-mentioned objects is also made by a composite obtainable by the process described above, this composite preferably having the same properties as the composite according to the invention described above.

A further contribution towards achieving at least one of the above-mentioned objects is made by chemical products comprising the superabsorbers according to the invention or a composite according to the invention. Preferred chemical products are, in particular, foams, shaped articles, fibers, foils, films, cables, sealing materials, liquid-absorbing hygiene articles, in particular diapers and sanitary napkins, carriers for plant or fungal growth regulating agents or plant protection active compounds, additive for building materials, packaging materials or soil additives.

The use of the superabsorbers according to the invention or of the composite according to the invention in chemical products, preferably in the above-mentioned chemical products, in particular in hygiene articles, such as diapers or sanitary napkins, and the use of the superabsorber particles as carriers for plant or fungal growth-regulating agents or plant protection active compounds also make a contribution towards achieving at least one of the above-mentioned objects. When used as carriers for plant or fungal growth-regulating agents or plant protection active compounds, it is preferable for the plant or fungal growth regulating agents or plant protection active compounds to be able to be released over a period of time controlled by the carrier.

The invention will now be explained in more detail with the aid of non-limiting figures and examples.

BRIEF DESCRIPTION OF THE DRAWINGS

FIG. 1 shows a particular embodiment of the device according to the invention for the production of superabsorbers in cross-section. In the polymerization region 1 a polymer gel is formed by free-radical polymerization from an aqueous monomer solution comprising partly neutralized acrylic acid, at least one crosslinking agent and initiators, and is then, optionally after prior comminution of the gel, dried in a drying region 2, preferably down to a water content of less than 10 wt. %. The water-absorbing precursor obtained in this manner can then first be post-crosslinked in a post-crosslinking reactor 3, optionally after further grinding and sieving to a particular particle size fraction, but it is also conceivable to feed the water-absorbing product directly to the further treatment region.

The further treatment region 4 can comprise a further, preferably heatable mixer 5 in which the water-absorbing precursor and a modifying agent, preferably a modifying agent which, if it is not added as the pure substance, is preferably in the form of an aqueous solution, an aqueous dispersion or an aqueous emulsion, are mixed. However, it is also conceivable for the modifying agent first to be added in the rotating container 6 via the feed 13. The modifying agent can optionally be added in a proportion in an upstream mixer 5 and in a proportion via the feed 13.

Figure 1:
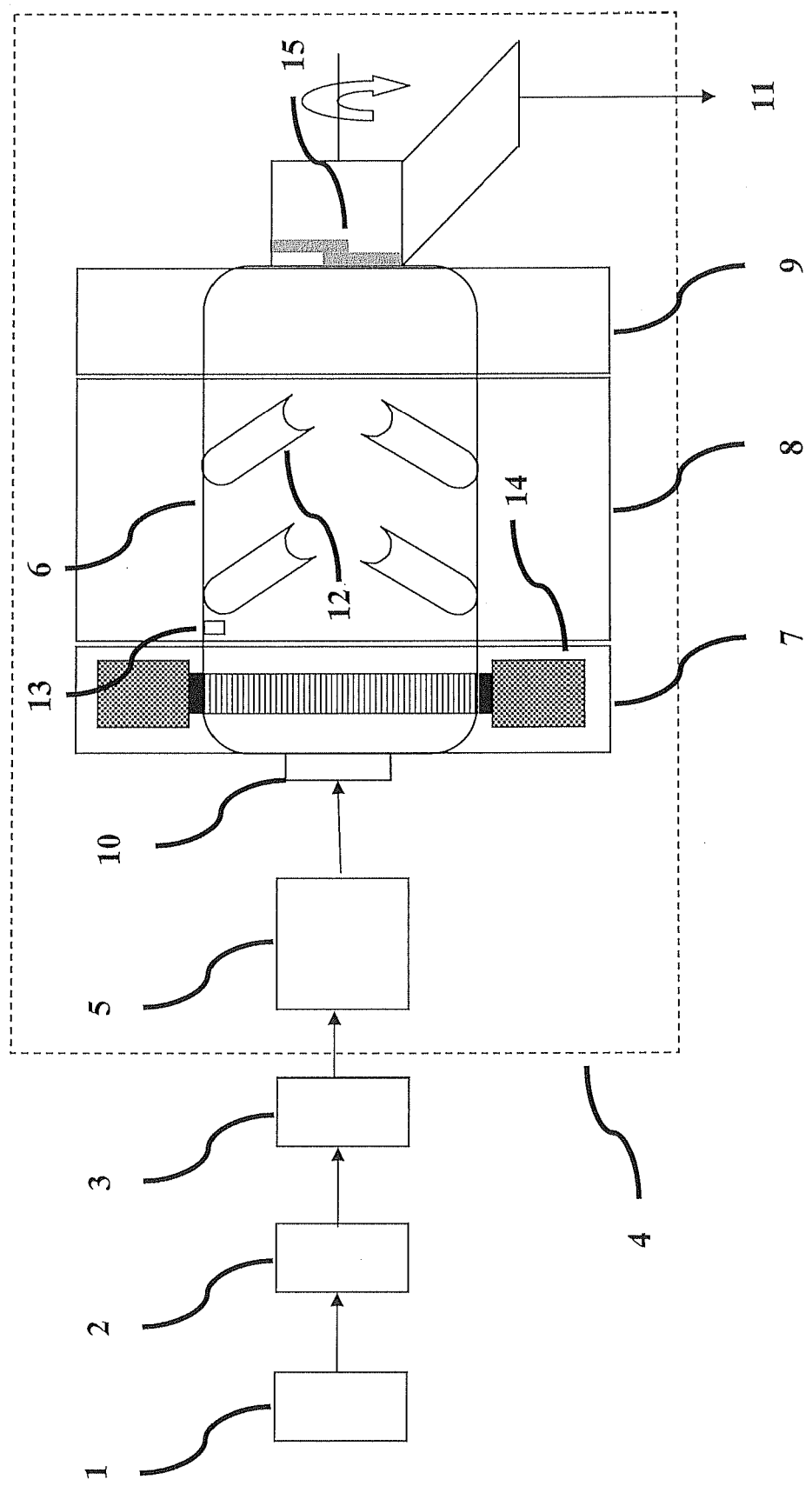
FIG. 1 shows a particular embodiment of the device according to the invention for the production of superabsorbers in cross-section.

In the rotating container 6 the water-absorbing polymer structure which has been brought into contact with the modifying agent is further treated by mixing. The rotating container comprises a front top region 7 in which the product inlet 10 is also located, a jacket region 8 and a rear top region 9 in which the product outlet 11 is also located. Inside the rotating container mixing aids in the form of paddles 12 which render possible thorough mixing of the water-absorbing polymer structure during horizontal rotation of the container 6 (see the arrow on the right in FIG. 1) are arranged permanently on the inside of the rotating container. The rotation of the container is rendered possible by the action of force from the motors 14.

Figure 4:
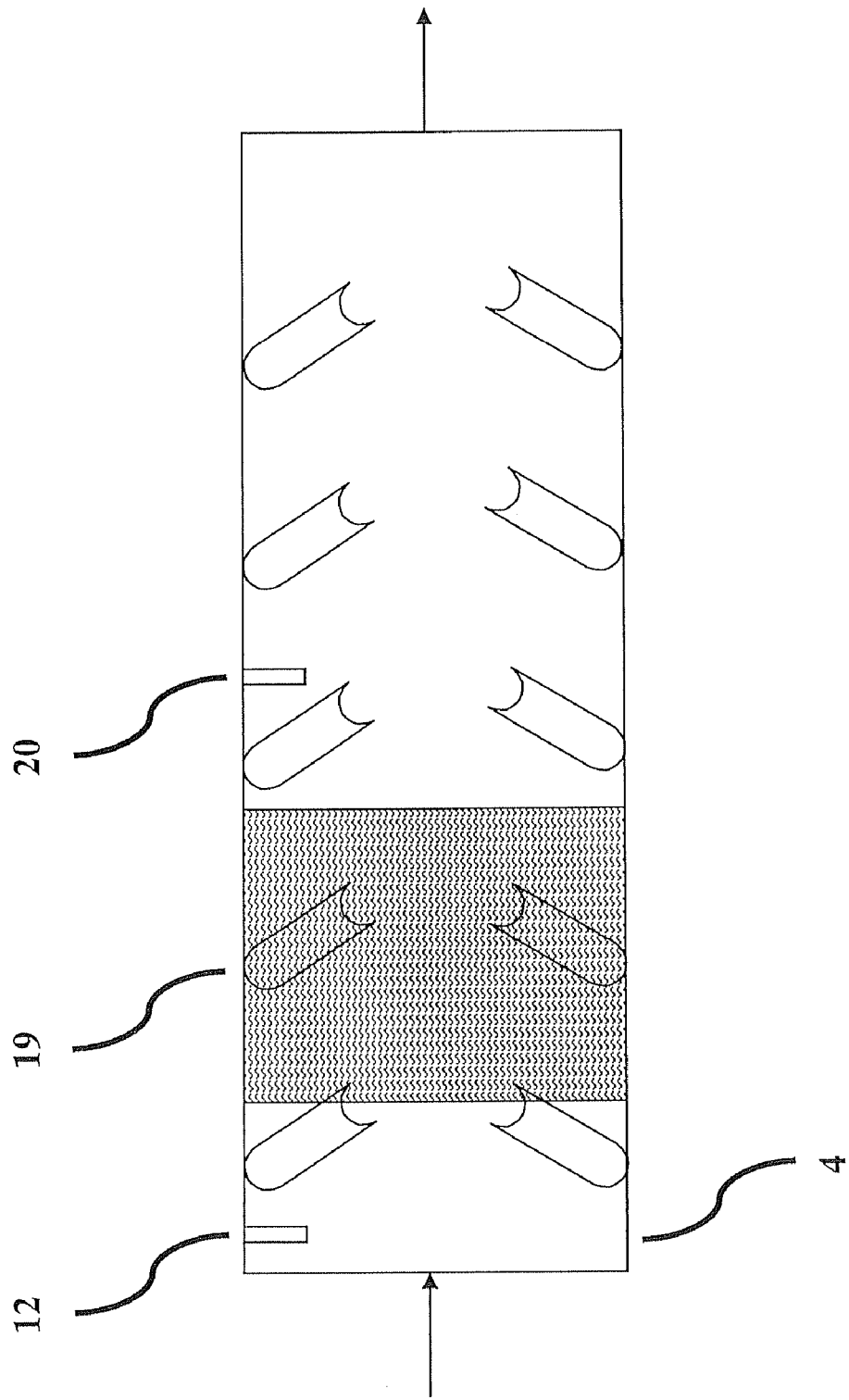
FIG. 4 shows a particular embodiment of the process according to the invention for the production of superabsorbers.

According to a particularly preferred embodiment of the device according to the invention, this comprises in the outlet region 10 a weir 15 as part of an outlet unit, the cross-sectional area of which can be regulated (in this context see also FIG. 4).

Figure 2:
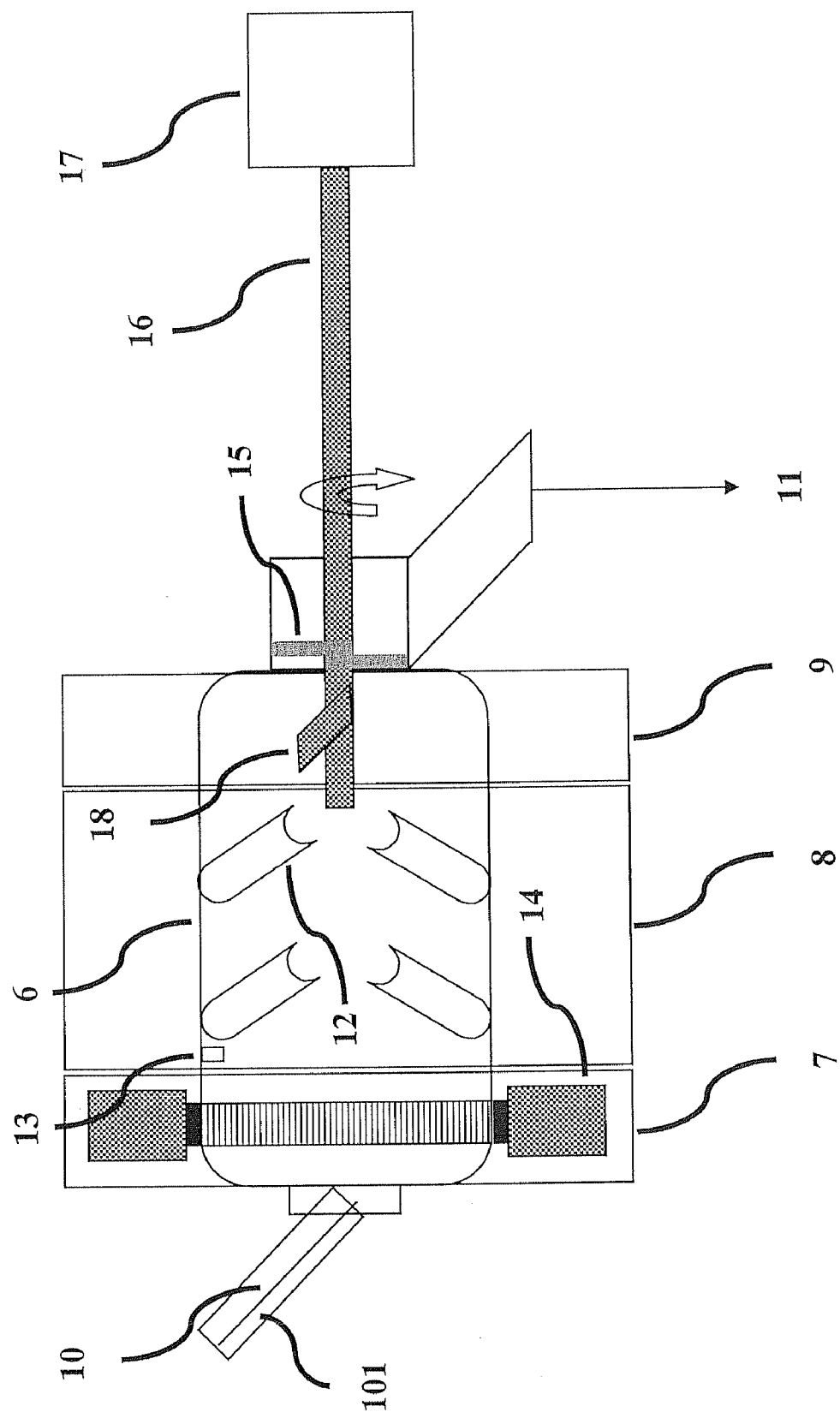
FIG. 2 shows a further embodiment of the device according to the invention for the production of superabsorbers in cross-section.

FIG. 2 shows a further embodiment of the device according to the invention for the production of superabsorbers in cross-section. According to this particular embodiment the further treatment region additionally comprises a lance 16 which can be guided in and out of the container 6 along the axis of rotation of the rotating container 6 by means of the servomotor 17. A discharge element 18 which can promote discharge of the product via the outlet 11 can be attached, for example, to this lance 16. The product inlet 10 is moreover configured as an inclined guiding means, such as a tube or a chute. The angle of inclination, like the entire configuration of the product inlet 10, should be chosen such that adhering of the material introduced into the rotatable container 6 or formation of lumps thereof is as far as possible avoided. A design of the inlet 10 with as little dead space as possible also contributes towards this. A conveying element 101, such as a shaker, conveyor belt or slide valve or a combination of at least two of these, can moreover be provided in the inlet 10.

Figure 3:
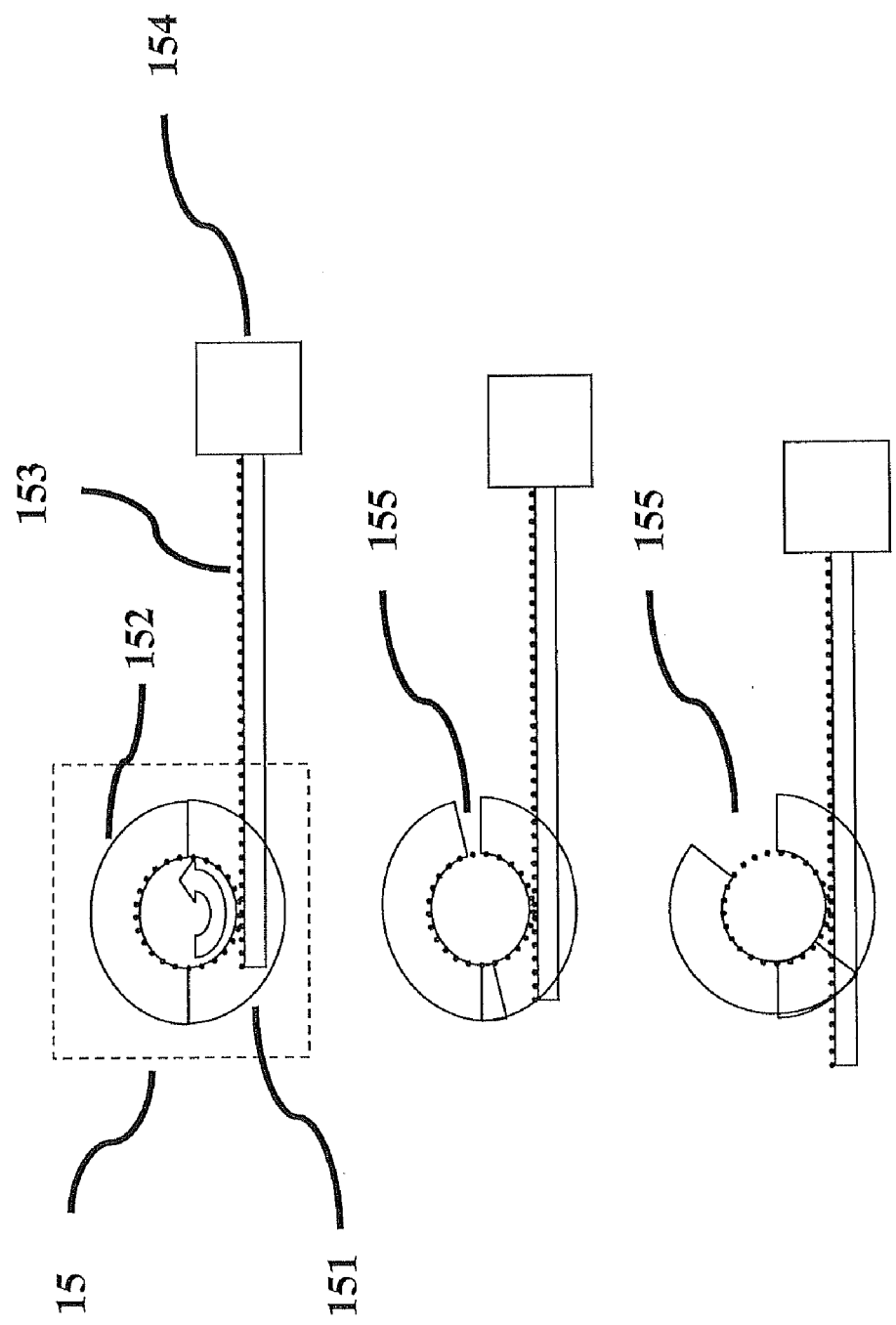
FIG. 3 shows a particular embodiment of a weir as a rotating plate weir in cross-section.

FIG. 3 shows a particular embodiment of a weir 15 in cross-section. According to this particular embodiment of the weir this comprises a lower and an upper circular segment (151, 152), wherein the upper circular segment 152 can be rotated about the central point of the circle formed by the upper circular segment 151 and the lower circular segment 152. This rotation can take place, for example, via a lance 153 which can be moved by means of a servomotor 154. When the upper circular segment 152 is rotated, a gap 155 forms, via which the water-absorbing product can be discharged from the rotating container. The amount of material exiting can thus be regulated via the width of the gap.

FIG. 4 shows a particular embodiment of the process according to the invention for the production of superabsorbers. According to this embodiment, a water-absorbing polymer structure is introduced into a rotating container 4, the water-absorbing polymer structure being brought into contact with a first modifying agent via a first feed 12 in the top region of the rotating container 4. If this first modifying agent is a surface post-crosslinking agent, it may be advantageous for the rotating container 4 to include, downstream of the feed of the surface post-crosslinking agent, a heatable region 19 in which the water-absorbing polymer structure is heated in order to effect the post-crosslinking. The post-crosslinked product then passes a further feed 20 in which a further modifying agent can be added, a corresponding further treatment then taking place during further passage of the water-absorbing polymer structure due to the rotation of the container and the resulting mixing of the superabsorber which has been brought into contact with the further modifying agent.

Figure 5:
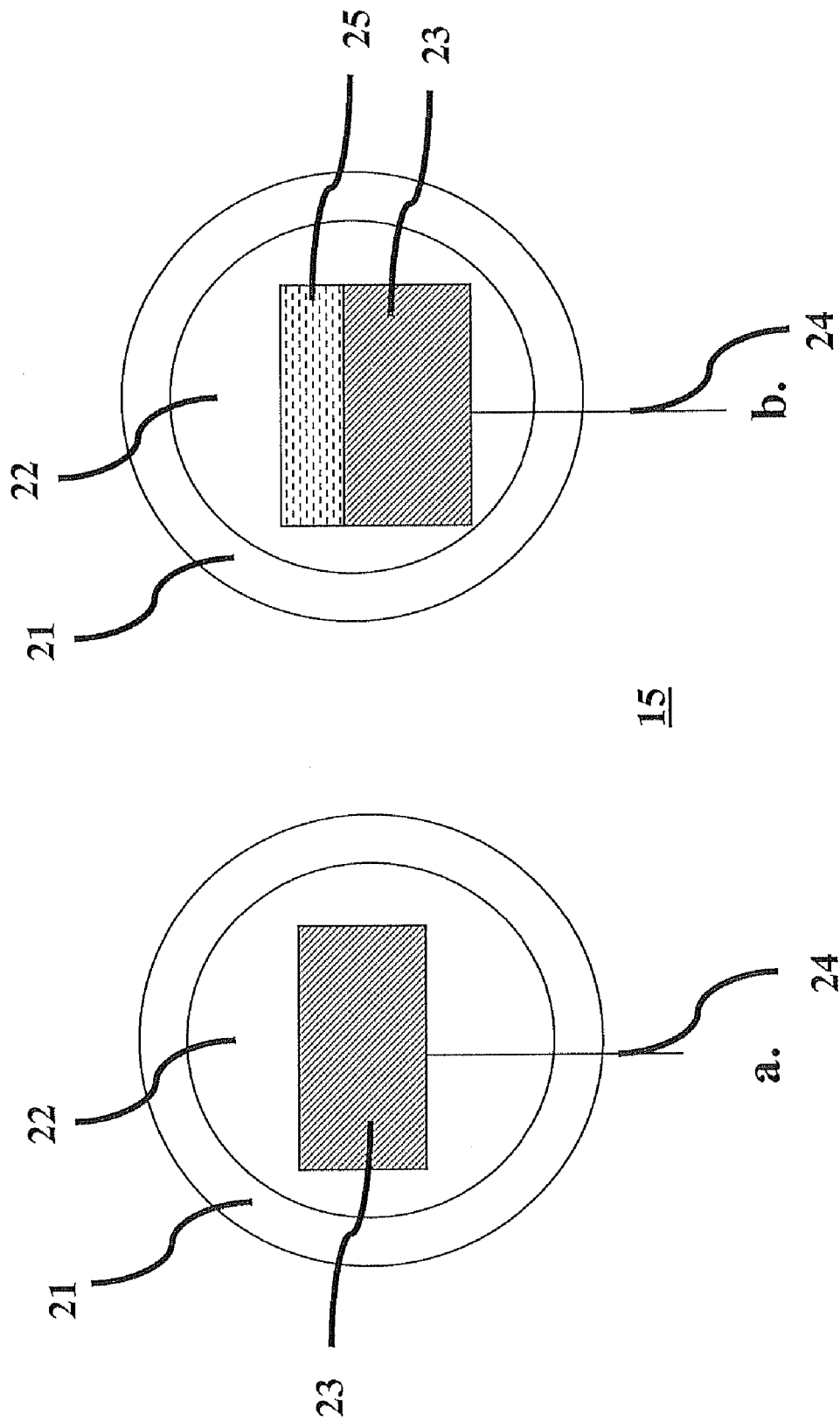
FIG. 5 shows a particular embodiment of a weir as a vertical weir in cross-section.

FIG. 5 shows a vertical weir as a further embodiment of a weir 15 according to the invention. An outlet opening mounting 21 provided in the exit opening region of the rotatable container 6 accommodates a plate-shaped outlet plate 22 mounted rotatably therein and having a rectangular exit opening 25. This has a rectangular outlet slide valve 23 which is mounted movably and is positively adjacent to one surface of the outlet plate 22. An outlet slide valve drive 24 is provided for moving the outlet slide valve 23. In part a. the outlet slide valve 23 closes the exit opening 25, and in part b. the outlet slide valve 23 is displaced and exposes the outlet opening 25, so that the rotatable container 26 can empty down to the lower mark of the outlet opening 25.

Figure 6:
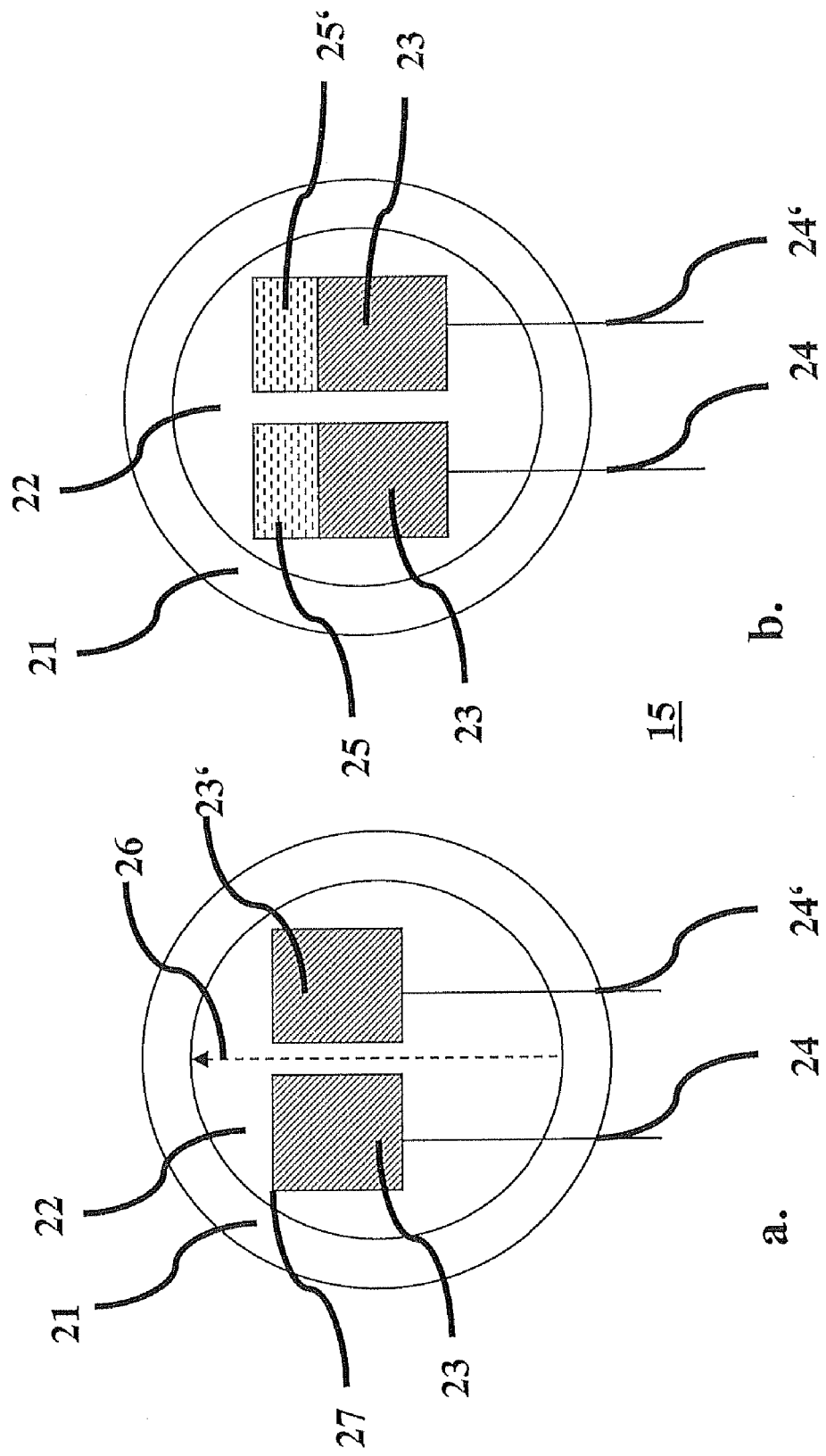
FIG. 6 shows a particular embodiment of a weir as a multiple weir in cross-section.

FIG. 6 shows a multiple vertical weir having two vertical weirs as a further embodiment of a weir 15 according to the invention. With reference to the statements relating to FIG. 5, it is additionally mentioned that the description for the single weir in FIG. 5 also applies to the two vertical weirs, the second weir being described by the functions identified with reference symbols with an apostrophe. As is also the case for the vertical weir according to FIG. 5, in the case of the multiple vertical weir it is also preferable for a weir height 27 resulting from the upper edge of the exposable exit opening 25, based on a weir height line 26 resulting from the maximum diameter of the outlet plate 22, to make up at least 30%, preferably at least 50% and particularly preferably at least 60% of the height of the weir height line 26.

Test Methods

General

Unless other test methods are given in the following, the test methods which are generally known to the person skilled in the art and appear to be conventional are used, test methods of EDANA (European Diaper and Nonwoven Association), which are generally mentioned as "ERT methods", being used in particular.

Determination of the "Free Swell Rate" (FSR)

This test method, which indicates the rate of absorption, was used for the determination in accordance with the method described in U.S. Pat. No. 5,149,335 (Kellenberger et al.), the test method of which is incorporated herein by reference.

Determination of the Dust Content

The dust content is determined with an apparatus from AnaTec Deutschland GmbH, Germany, of the type "Dust MON L". For this, a sample of 30.00 g was introduced into a funnel tube. At the start of the measurement a funnel valve open automatically and the sample falls into a dust reservoir. The reduction in a laser beam (decrease in transmission) due to the dust formation is now measured. This value serves to determine the dust content. The dust content (STZ) is obtained from a maximum value at the start of the measurement and a dust value measured after 30 seconds for determination of the suspended content. The dust content thus results from the sum of the maximum value and the dust value.

Determination of the Water Content

The WDS 400 System 239 from Sartorius® is used for determination of the water content. The WDS 400 measuring apparatus is operated by a computer program (WDS 400 version 2.1.8). The chemical sodium tungstate 2-hydrate is used as the standard. The gas flow of the apparatus is first checked with the aid of a scale and adjusted to 2 ccm/min. The WDS 400 System is heated thoroughly before a measurement. Before the thorough heating sample boats in the oven are removed with forceps. The further thorough heating operation is controlled by the computer program. After thorough heating to 400° C. and cooling to below 40° C., a tare and standard measurement are performed. For this, a sample boat is first inserted into the apparatus with forceps and the tare of a boat is then determined for the standard. This measurement operation is likewise controlled by the computer program, an increase in temperature occurring. After this measurement operation the WDS System is cooled again to below 40° C. and the boat is removed. The exact weight (approx. 20 mg) of the product subsequently to be analyzed is entered into the computer program. After the boat has been introduced again with the forceps, the measurement is started. The computer program controls the predetermined course of the temperature with respect to time. In a first time section in the range from t=0 to t=2 min the temperature is 80° C. In a second time section in the range between t=2 min and t=4 min the temperature is increased uniformly from 80° C. to 200° C. In a third time section in the range from t=4 min to t=7 min the temperature is kept constant at 200° C. In a fourth time section in the range between t=7 min to t=8 min the temperature is increased uniformly from 200° C. to 300° C. Thereafter, the temperature in a fifth time section up to the end of the measurement, which is at t=25 min, is kept constant at 300° C. The measurement results are evaluated by the computer program and plotted by means of a curve on a current/time graph. The curve shows the amount of water which has evaporated at a certain point in time, this being proportional to the current measured at that time. The integral below the curve from t=0 to t=$t_1$ is proportional to the surface water, wherein $t_1$ is the relative minimum before the last maximum of the total curve. The core water is obtained from the integral of the curve from $t_1$ up to the end of the measurement after 25 minutes, calculated from the first increase in temperature $T_1$.

Measurement of the FFC Value

The FFC value provides information on the flow properties of bulk goods in a silo. The ring shear tester RST-O1.O1 from Dr. Ing. Dietmar Schulze Schiiligutmessteclmik in D-38302 Wolfenbuttel is used for the measurement. The RST apparatus is connected to a computer programmed with RST Control 95 software and a printer for control and for printing out the measurement results. The ring shear tester has the following settings for standard product analyses: During initial shear a pressure of 500 Pa is used. During the shearing off pressures of 100 Pa, 250 Pa, 400 Pa and 100 Pa are used. After the standard shear cell of the apparatus has been mounted on the apparatus with the cover, the zero values of the force measurement are tested. The desired product-specific measurement method will be selected in the computer program. This is effected first with a standard measurement (conditions as described above). The shear cell is then filled with water-absorbing polymer structure as bulk goods, a smooth surface being ensured. Thereafter, the shear cell is weighed together with the bulk goods. The weight of the shear cell including the bulk goods is then entered into the computer program. For the standard measurement a pressure of 500 Pa is used for the initial shear. A pressure of 100 Pa, 250 Pa, 400 Pa and 100 Pa is used for the shearing off. After the measurement has been carried out, the measurement results are determined by the computer program and evaluated in accordance with pages 5 and 6 of the instructions from Dr, Ing. Dietmar Schulze under "HOME—www.dietmar-schulze.de", status 12 Mar. 2004.

Wall Friction Angle

The wall friction describes the friction between bulk goods and a wall material used. The measurement is carried out at a room temperature of between 18-23° C. A ring shear tester from Dr. Ing. Dietmar Schulze Schuttgutmesstechnik in D-38302 Wolfenbuttel is employed for measurement of the wall friction. The base ring of the shear tester is replaced by the wall material which is to be investigated. The measurement cell is then filled with water-absorbing polymer structure as bulk goods in the shear tester. A force generated by the ring shear tester and acting perpendicular to the wall material to be investigated causes the normal stress $\sigma_w$. The shearing force which is needed to shift the bulk goods under the action of the normal stress and which acts perpendicular to the normal force and generates the shear stress $\tau_w$, is then measured. This shear stress is determined by dividing the shearing force measured by the size of the wall area on which the shearing force acts. For a given normal stress $\sigma_w$ the associated shear stress $\tau_w$ is stated in this way. The wall friction angle $\phi_x$ can be determined from this pair of values by inserting the parameters into the following relationship:

$$\tan(\phi_x) = \tau_w / \sigma_w$$

and performing the evaluation in accordance with pages 11 and 12 of the instructions of Dr. Ing. Dietmar Schulze under "HOME—www.dietmar-schulze.de", status 12 Mar. 2004.

EXAMPLES

Example 1

2 wt. % of water was added, as a modifying agent, to a water-absorbing polymer structure (the product Favor® SXM 9300 obtainable from Evonik Stockhausen GmbH, Krefeld) in a Drais® mixer of the type K-TT 4E with an average dwell time in the mixer of approx. 30-60 sec, which was operated at 900 revolutions per minute. The resulting polymer structure with the modifying agent is to be described as ground-damp. The polymer structure treated in this way is then transferred with a product introduction of 80 kg/h into a Lindor mixer, which was operated at 4.75 revolutions per minute. During the filling phase the weir was closed. The weir was then opened stepwise until a product discharge of 1.82 kg/min was established. The modified polymer structure obtained in this way is free-flowing and does not differ externally from the starting substance. The properties before and after the treatment are shown in Table 1 as the mean of in each case three samplings.

TABLE 1

| Product | Surface water | Core water | Total water | Dust content | FSR |
| --- | --- | --- | --- | --- | --- |
| SXM 9300 | 2.3% (39%)* | 3.5% (61%) | 5.8% | 1.2 | 0.2 |
| Ex drum mixer | 3.5% (47%) | 3.8% (53%) | 7.3% | 0.7 | 0.2 |

*= corresponds to the content in the total water

By the treatment by the process according to the invention, a very uniform distribution of the modifying agent can be achieved with a relatively low tendency towards dusting and swelling properties which remain constant.

Example 2

As described in Example 1, a water-absorbing polymer structure (the product Favor® SXM 9155 obtainable from Evonik Stockhausen GmbH, Krefeld) was treated with 2 wt. % of water as a modifying agent in a Drais® mixer and the mixture was fed to a Lindor mixer. After the filling phase the weir was adjusted such that an equilibrium was established between product flowing in and flowing out of the Lindor mixer of approx. 80 kg/h. Table 2 shows a small particle range of the particle size distribution according to sieve analysis before and after the treatment.

TABLE 2

| | product | |
| --- | --- | --- |
| Particle size | Favor ® SXM 9155 | Ex drum mixer |
| >300 µm | 13.5% | 13.5% |
| >200 µm | 14.7% | 13.4% |
| >100 µm | 7.2% | 7.0% |
| <100 µm | 0.7% | 0.9% |

It can be seen from Table 2 that the amount of particles having small particle sizes remains substantially constant. The particularly gentle mixing of the process according to the invention is shown by this means.

Example 3

2 wt. % of water, as a modifying agent, was added to a water-absorbing polymer structure (the product Favor® SXM 9155 obtainable from Evonik Stockhausen GmbH. Krefeld) by means of the nozzle in a Lindor mixer. After the filling phase the weir was adjusted such that an equilibrium was established between product flowing in and flowing out of the Lindor mixer of approx. 80 kg/h. Table 3 shows a small-particle range of the particle size distribution according to sieve analysis before and after the treatment.

TABLE 3

| Particle size | product | |
|---|---|---|
| | Favor ® SXM 9155 | Ex drum mixer |
| >300 μm | 12.9% | 12.7% |
| >200 μm | 12.0% | 11.3% |
| >100 μm | 4.6% | 4.2% |
| <100 μm | 0.2% | 0.4% |

It can be seen from Table 3 that the amount of particles having small particle sizes remains substantially constant. The particularly gentle mixing of the process according to the invention is shown by this means.

Example 4

As described in Example 1, a water-absorbing polymer structure (the product Favor® SXM 9155 obtainable from Evonik Stockhausen GmbH. Krefeld) was treated with 10 wt. % of a 50% strength citric acid solution and 1.0% of a precipitated silica (Sipernat) as a modifying agent in a Drais® mixer and the mixture was fed to a Lindor mixer. After the filling phase the weir was adjusted such that an equilibrium was established between product flowing in and flowing out of the Lindor mixer of approx. 80 kg/h. The modified superabsorber obtained in this way is free-flowing. Because of the high amount of liquid and the tacky property of the citric acid, without very good thorough mixing in the Lindor mixer the slightly swollen polymer structure, which is extremely lumpy, moist and tacky, cannot be further processed in a conventional mixer in a manner which is appropriate on a large industrial scale.

Example 5

As described in Example 1, a water-absorbing polymer structure (the product Favor® SXM 9155 obtainable from Evonik Stockhausen GmbH. Krefeld) was treated with 5 wt. % of a 33% strength Tegosorb® A30 solution and 0.5% of a precipitated silica (Sipernat) as a modifying agent in a Drais® mixer and the mixture was fed to a Lindor mixer. After the filling phase the weir was adjusted such that an equilibrium was established between product flowing in and flowing out of the Lindor mixer of approx. 80 kg/h. The following characteristic data were obtained before and after the Lindor mixer. Because of the high amount of liquid having a slightly oily consistency, without very good thorough mixing in the Lindor mixer the slightly swollen polymer structure, which is extremely lumpy and moist, cannot be further processed in a conventional mixer in a maimer which is appropriate on a large industrial scale. The properties of the superabsorber obtained in this way are shown in Table 4.

TABLE 4

| | FFC value: | |
|---|---|---|
| | Before the Lindor mixer | After the Lindor mixer |
| Sample 1 | 4.5 | 6.2 |
| Wall friction angle | 11.4 | 11.8 |

It can be seen that a clear improvement in the free-flowing properties, characterized by the FFC value, with continuing good wall friction was achieved.

LIST OF REFERENCE SYMBOLS

| | |
|---|---|
| 1 | Polymerization region |
| 2 | Drying region |
| 3 | Surface post-crosslinking reactor |
| 4 | Further treatment region |
| 5 | Further mixer |
| 6 | Rotating container |
| 7 | Front top region of the rotating container |
| 8 | Jacket region of the rotating container |
| 9 | Rear top region of the rotating container |
| 10 | Product inlet |
| 101 | Conveying element |
| 11 | Product outlet |
| 12 | Paddle |
| 13 | Feed for a modifying agent |
| 14 | Motor |
| 15 | Weir |
| 151 | Lower circular segment of the weir |
| 152 | Upper circular segment of the weir |
| 153 | Lance for regulating the weir |
| 154 | Motor for horizontal movement of the lance 143 |
| 155 | Opened gap in the weir through which the superabsorber can exit from the rotating container |
| 16 | Lance for displacing a discharge element inside the rotating container |
| 17 | Motor for horizontal movement of the lance 15 |
| 18 | Discharge element |
| 19 | Heatable or coolable region |
| 20 | Further feed for a modifying agent |
| 21 | Outlet opening mounting |
| 22 | Outlet plate |
| 23 | Outlet slide valve |
| 24 | Outlet slide valve drive |
| 25 | Exit opening |
| 26 | Weir height line |
| 27 | Weir height |

The invention claimed is:

1. A process for the production of a superabsorber, comprising as steps:
    a) providing a water-absorbing crosslinked polymer structure;
    b) bringing the water-absorbing crosslinked polymer structure into contact with a modifying agent; and
    c) further treating the water-absorbing crosslinked polymer structure which has been brought into contact with the modifying agent;
    wherein process steps b and c) are carried out at least in part in a rotating container comprising a horizontally mounted container constructed like a drum, which can be made to rotate around an axis running horizontally through the middle of the container by suitable means and wherein said horizontally mounted container comprises an inlet feed for said modifying agent, wherein said polymerization region, said drying region, and said further treatment region are in communication with one another by fluid lines.

2. The process according to claim 1, wherein the water-absorbing crosslinked polymer structure provided in process step a) has a water content of at most about 20 wt. %, based on the total weight of the water-absorbing polymer structure.

3. The process according to claim 1, wherein step c) is carried out continuously.

4. The process according to claim 1, wherein the modifying agent is chosen from a solution, a dispersion, an emulsion, and a powder.

5. The process according to claim 1, wherein the water-absorbing crosslinked polymer structure is post-crosslinked on the surface.

6. The process according to claim 1, wherein the water-absorbing crosslinked polymer structure flows through the rotating container.

7. The process according to claim 1, wherein the rotating container is filled to at most about 80% of the largest cross-sectional area of the rotating container.

8. The process according to claim 7, wherein the rotating container is at least partly configured in the form of a drum.

9. A device for the production of a superabsorber comprising:
   a polymerization region;
   a drying region; and
   a further treatment region;
wherein said further treatment region comprises a rotatable container comprising a horizontally mounted container constructed like a drum, which can be made to rotate around an axis running horizontally through the middle of the container by suitable means and wherein said horizontally mounted container comprises an inlet feed for a modifying agent and wherein said rotatable container comprises a movable discharge element wherein said discharge element is in communication with a lance which may be guided in and out of said rotatable container along an axis of rotation of the rotating container; and
   wherein said polymerization region, said drying region, and said further treatment region are in communication with one another by fluid lines.

10. A process for the production of a superabsorber, comprising as steps:
   a) providing a water-absorbing crosslinked polymer structure;
   b) bringing the water-absorbing crosslinked polymer structure into contact with a modifying agent; and
   c) treating the water-absorbing crosslinked polymer structure which has been brought into contact with the modifying agent in a step of further treatment;
   wherein said further treatment is carried out in a device comprising:
      a polymerization region;
      a drying region; and
      a further treatment region;
   wherein said further treatment region comprises a rotatable container comprising a horizontally mounted container constructed like a drum, which rotates around an axis running horizontally through the middle of the container by suitable means and wherein said horizontally mounted container comprises an inlet feed for said modifying agent and wherein said rotatable container comprises a vertically adjustable weir; and
   wherein said polymerization region, said drying region, and said further treatment region are in communication with one another by fluid lines.

11. The process according to claim 10, wherein the superabsorber comprises an inner region and an outer region surrounding the inner region, and wherein said modifying agent is found in the outer region of the superabsorber.

12. The process according to claim 1, wherein said modifying agent is selected from water, a solution, a dispersion, an emulsion or a powder.

13. The process according to claim 12, wherein said modifying agent comprises at least 50 wt % water based on the total weight of the modifying agent.

14. The device of claim 9, wherein said modifying agent is selected from water, a solution, a dispersion, an emulsion or a powder.

15. The device of claim 14, wherein said modifying agent comprises at least 50 wt % water based on the total weight of the modifying agent.

16. The process according to claim 10, wherein said modifying agent is selected from water, a solution, a dispersion, an emulsion or a powder.

17. The process according to claim 16, wherein said modifying agent comprises at least 50 wt % water based on the total weight of the modifying agent.

* * * * *

UNITED STATES PATENT AND TRADEMARK OFFICE
CERTIFICATE OF CORRECTION

PATENT NO. : 8,349,913 B2  
APPLICATION NO. : 12/600964  
DATED : January 8, 2013  
INVENTOR(S) : Jörg Harren et al.

Page 1 of 1

It is certified that error appears in the above-identified patent and that said Letters Patent is hereby corrected as shown below:

Title Page, correct the Inventors data in item (75) with the following paragraph.

-- Inventors: Jörg Harren, Krefeld (DE); Herbert Vorholt, Haltern am See (DE); Manfred Van Stiphoudt, Kempen (DE); Rüdiger Hose, Tönisvorst (DE); Stephan Ramlow, Krefeld (DE); Stefan Derstappen, Tönisvorst (DE); Axel Busch, Krefeld (DE); Michael Lange, Rheinberg (DE); Waldemar Inger, Krefeld (DE); Kal Hebben, Tönisvorst (DE) --.

Signed and Sealed this
Nineteenth Day of February, 2013

Teresa Stanek Rea
*Acting Director of the United States Patent and Trademark Office*